(12) United States Patent
Martin

(10) Patent No.: US 12,064,400 B1
(45) Date of Patent: *Aug. 20, 2024

(54) METHOD AND SYSTEM FOR REDUCING ACTIVE INGREDIENT POTENCY IN PAIN-MANAGEMENT COMPOSITIONS TO A QUARTER AMOUNT OF APPROVED LEVELS

(71) Applicant: Luduss, LLC, Garden City, NY (US)

(72) Inventor: Curtis J. Martin, Garden City, NY (US)

(73) Assignee: Luduss, LLC, Garden City, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/087,680

(22) Filed: Dec. 22, 2022

(51) Int. Cl.

| | | |
|---|---|---|
| *A61K 31/05* | (2006.01) |
| *A61K 9/20* | (2006.01) |
| *A61K 9/48* | (2006.01) |
| *A61K 31/137* | (2006.01) |
| *A61K 31/167* | (2006.01) |
| *A61K 31/192* | (2006.01) |
| *A61K 31/4402* | (2006.01) |
| *A61K 31/4468* | (2006.01) |
| *A61K 31/451* | (2006.01) |
| *A61K 31/485* | (2006.01) |
| *A61K 31/616* | (2006.01) |
| *A61K 36/185* | (2006.01) |
| *A61K 45/06* | (2006.01) |

(52) U.S. Cl.
CPC ............ *A61K 31/05* (2013.01); *A61K 9/2068* (2013.01); *A61K 9/2095* (2013.01); *A61K 9/4833* (2013.01); *A61K 9/4875* (2013.01); *A61K 31/137* (2013.01); *A61K 31/167* (2013.01); *A61K 31/192* (2013.01); *A61K 31/4402* (2013.01); *A61K 31/4468* (2013.01); *A61K 31/451* (2013.01); *A61K 31/485* (2013.01); *A61K 31/616* (2013.01); *A61K 36/185* (2013.01); *A61K 45/06* (2013.01)

(58) Field of Classification Search
CPC .. A61K 31/105; A61K 31/137; A61K 31/167; A61K 9/2068
See application file for complete search history.

(56) References Cited

U.S. PATENT DOCUMENTS

2020/0289431 A1* 9/2020 KuusReichel ......... A61K 31/05

* cited by examiner

*Primary Examiner* — Kevin E Weddington
(74) *Attorney, Agent, or Firm* — Patent Law Works LLP

(57) ABSTRACT

A system and method for producing pain-management formulations that amplify and improve the effects of lower doses of the active ingredients in existing pain-management medications is disclosed. Active ingredients in medications are combined in smaller doses, for example, 25% of typical approved or prescribed doses with a natural ingredient used to amplify the effects of the active ingredient without adversely affecting a human's organs. In one embodiment, the combined formulation comprises an active drug ingredient, for example naproxen, combined with a designated amount of a natural ingredient in a symbiotic relationship in a natural USP grade carrier oil to formulate a blended composition that is effective yet safe. The symbiotic relationship between the synthetic and natural ingredients serve to amplify the effects of the active synthetic ingredient for pain management while preventing the adverse effects caused by increased medication potency on a human body's organs.

11 Claims, 35 Drawing Sheets

200B

Hydrocodone bitartrate

CBD Isolate

1600

Morphine

+

CBD Isolate

2200

Fentanyl Citrate

CBD Isolate

2500

Fentanyl

CBD Isolate

2600

METHOD AND SYSTEM FOR REDUCING ACTIVE INGREDIENT POTENCY IN PAIN-MANAGEMENT COMPOSITIONS TO A QUARTER AMOUNT OF APPROVED LEVELS

BACKGROUND

1. Field of the Invention

The present invention relates generally to the field of managing pain and human discomfort by use of oral compositions for pain-management therapy and care. More particularly, the present invention relates to a system and method that amplifies the beneficial effects of lower dosages of active synthetic ingredients used in pain-management compositions. The present invention improves human reactions to a low dose of active synthetic ingredients in pain-management formulations. The present invention also relates to producing new and improved pain-management compositions or formulations that blend active synthetic ingredients with a natural ingredient in a symbiotic relationship. The present invention relates to an improved pain-management oral composition with a ratio of 0.25 of an active synthetic ingredient amount in typical prescribed doses with a designated amount of a natural ingredient to formulate a blended composition that is effective yet safe. This serves to amplify the effects of the active synthetic ingredient composition in order to prevent the adverse effects caused by increased medication potency on a human body's organs.

2. Description of the Related Art

Physical pain and human discomfort are experienced by many in all spheres of life. As one example, use of medications and non-pharmacological strategies to relieve and prevent pain and discomfort is widespread in sport. It is common knowledge that elite athletes use prescription and over-the-counter analgesics to prevent or relieve pain upon being injured. These analgesics typically include oral non-steroidal anti-inflammatory drugs ("NSAIDs"), injectable NSAIDs, other non-opioid analgesics, opioid analgesics, injectable and transdermal anesthetics, and other medications and over-the-counter supplements.

Pain management involves a general understanding of pain physiology, including the types of pain humans experience. Pain is an unpleasant sensory and emotional experience associated with actual or potential tissue damage. Typically, pain is classified as nociceptive, neuropathic or nociplastic/algopathic/nocipathic. Nociceptive pain refers to pain clearly associated with tissue damage or inflammation. This type of pain is most commonly associated with a sport injury. Inflammatory pain is a type of nociceptive pain that results from the activation and sensitization of nociceptors by inflammatory mediators and is common in acute traumatic sport injury with related swelling and inflammation. Neuropathic pain results from a lesion or disease in the somatosensory nervous system and is common in Paralympic athletes with spinal cord injury.

Another type of pain common among humans is chronic pain. Humans suffer from chronic pain that is neither nociceptive nor neuropathic, but associated with clinical and psychophysical findings (hypersensitivity) that suggest altered nociceptive functioning (e.g., as in fibromyalgia, non-specific low back pain, or the like). These are also sometimes described as nociplastic, algopathic and nocipathic pain.

Experts opine that pain in the immediate aftermath of most sport injuries is nociceptive associated with tissue damage, and that nociplastic/algopathic/nocipathic pain may develop after injury and is typically seen in athletes with chronic pain. Typically, a sports injury is defined as a new or recurring musculoskeletal issue sustained during competition or training that requires medical attention. Often, a sports injury may require restricted activity for at least one day. As one example, acute traumatic injury is a single event that leads to a singular macrotrauma on previously healthy tissue. Acute traumatic injury in an athlete may be accompanied by fear, anxiety and heightened cognitive focus on the injury. As another example, overuse injuries can occur from repetitive submaximal loading of the musculoskeletal system when inadequate recovery has not allowed structural adaptation to occur. In all instances, injury is the outcome of the difference between the volume and intensity of the stress or force applied to the body and the body's ability to dissipate this stress or force. Injury results from repetitive microtrauma imposed on otherwise healthy tissue or repeated application of lesser forces to already damaged tissue. In essence, when injured, athletes cannot train at an optimal workload to build physical capacity and resilience to the demands of the sport that they play.

In some scenarios, subacute recurrent injuries and chronic degenerative conditions may form a continuum with overuse injuries. A recurrent injury is an incident of the same type and at the same site linked to an index incident, which occurs after an athlete's return to full function and participation from the recorded index incident. Although degenerative conditions may develop independent of sport injury, some result from prior acute or repetitive overuse injuries and manifest as a chronic overuse injury.

Sports medicine commonly focuses on the diagnosis and management of a sport-related injury. Pain medicine focuses on the diagnosis and management of pain disorders. There are instances where injury may occur without pain and pain may present without evidence of injury. Pain management and injury management are not necessarily the same. Pain is a subjective experience dependent on complex interactions of neurobiological, cognitive, affective, contextual and environmental factors. Pain management typically depends on identifying contributory factors from biological, psychosocial, and contextual domains and addressing them through various evidence-based techniques. In some instances, physical therapy may be used to address pain problems, especially in subacute and chronic phases. Therapy may increase strength, stamina, and endurance, and may correct biomechanical contributors to pain and injury. Psychological strategies, which can begin immediately after injury, may also target pain management directly through training in skills such as muscle relaxation and imagery, as well as indirectly by identifying and addressing an athlete's worries and concerns, any comorbid mental health disorders and environmental factors relevant to recovery and return to play ("RTP"). Various modalities and massage have traditionally been the mainstays of physical therapy for pain management. Recent studies, however, show that many physical therapy techniques have no clear benefit beyond non-specific effects and natural history, with some exceptions.

In some instances, low-level laser therapy may be beneficial in treating tendinopathy and improving acute muscle recovery. Although cryotherapy is commonly used, there is little evidence from prospective studies assessing the benefit of this intervention. Ultrasound therapy may have a limited role in managing plantar fasciitis but has not demonstrated effectiveness in other studies. Electrical stimulation, massage therapy, myofascial trigger point treatments and acupuncture have also not shown reliable and consistent efficacy for relief of pain resulting from musculoskeletal injury.

In some instances, movement and exercise may have pain-relieving effects. Strength training and conditioning are sometimes effective as rehabilitation tools after injury. They can also be helpful in managing pain and reversing deconditioning in individuals with chronic painful conditions such as osteoarthritis, fibromyalgia and chronic musculoskeletal pain. Exercise can activate endogenous opioid and cannabinoid systems, induce an anti-inflammatory state and activate antinociceptive pathways. Isometric exercise can promote intracortical inhibition (which downregulates brain networks that subserve pain) and may offer significant pain-relieving benefits beyond those offered by isotonic and eccentric exercises for managing tendinopathy. Psychosocial interventions are also used with possible efficacy in sports rehabilitation include skills training in goal setting, imagery, relaxation and positive self-statements. Stress inoculation training can reduce anxiety, pain and days to recovery after arthroscopic surgery for meniscus injury. Yet other interventions relevant to athletes include cognitive restructuring (identifying and challenging negatively biased appraisals) and developing plans for maintaining treatment gains and coping with setbacks and pain flare-ups. These strategies are broadly categorized as cognitive-behavioral therapies ("CBTs"). CBT is the prevailing psychosocial treatment for chronic pain problems, and there is high-level evidence of its efficacy in reducing pain and pain-related disability in studies of non-athletes. Psychologically informed physical therapy, which incorporates cognitive and behavioral principles and strategies (e.g., techniques to reduce fear-avoidance, use of graded activity and exposure techniques), and education about pain during physical rehabilitation, is a promising approach with some evidence supporting its use.

It is well known that disordered sleep is common among athletes, both when recovering from injury and during the competition and training seasons. Sleep and pain have a reciprocal relationship—pain disturbs sleep, and poor sleep quality or duration increases pain levels in clinical populations and decreases pain thresholds in otherwise healthy people. Addressing sleep disorders could improve performance and the general health of the athlete. Psychological strategies including CBT, self-hypnosis and mindfulness-based stress reduction show significant potential to improve sleep in non-athletes. CBT for insomnia has demonstrated efficacy.

Persistent pain is influenced by any proinflammatory load, which makes nutrition possibly relevant to managing pain in athletes. However, studies demonstrating benefit from nutritional supplements are not methodologically sound and have unclear relevance to elite athletes. Furthermore, supplements are poorly regulated and may contain banned substances. Consequently, supplements cannot currently be recommended as part of pain management for elite athletes.

Elective surgery is not an option in the treatment of pain itself, but may address structural damage non-responsive to non-operative treatment, or to avoid further impairment of an athlete's health. An operation for a chronic injury and pain condition may aim to correct a structural problem that influences pain and functional limitations and should occur as part of a multifaceted, biopsychosocial management approach. Surgery is only performed to treat chronic pain simply because all other interventions have failed but should rather be used when a structural problem associated with the pain has been identified.

The prescription or provision of medication is most common to the management of pain in elite athletes. Analgesic medications are used in accordance with relevant regulations and the general guidelines for their safe and efficacious use. The core pharmacological principles of pain management in elite athletes include prescribing medication prescription is only one component of managing pain. Current medications by themselves do not address many instances of pain in athletes and the general population. Medications are prescribed at the lowest effective dose for the shortest period of time as they pose a critical risk as well with their many dangerous side effects, especially with extended use. They may not be tolerated by some, especially at high potency levels.

Recording athlete-reported severity of pain (e.g., with a numerical rating scale) can be useful in monitoring the effectiveness of a medication. Written documentation of each prescription is a basic standard of care. Although informed consent is fundamental in medical care, including those situations in which medication is prescribed, in many instances, athletes anxious to recover and return to play, seek quick and effective solutions. Thus, medications play a central role in the management of an athlete with acute pain who is considered for same-day return to play. Such medications may suffice for mild to moderate pain, but not for more severe pain. For moderate to severe pain, typically opioids may be used. Opioids may impair reaction time and other faculties.

Corticosteroid injections are typically not recommended for same day return to play and generally provide the same relief as that of local anesthetics, with side effects that cause acute muscle/tendon weakening, thereby increasing the chance of injury. Other injections, such as platelet-rich plasma ("PRP") and intra-articular viscosupplementation, do not provide immediate relief for same day return to play.

Moreover, medications prescribed for acute pain are typically not recommended for use more than five days. For pain that persists more than ten days, extended use of medications elevates the risks to the human body. In addition, different medications have different risk-benefit profiles.

When an athlete has severe acute pain, relief of pain is not only humane but necessary to facilitate early mobilization. For severe pain, when opioids are prescribed, many risks are inevitable, for example, risks of opioid dependence or addiction as well as overdose, especially if used in combination with alcohol or benzodiazepines. Opioid use beyond ten days adds substantial risks, for example, opioid use for more than seven days after painful musculoskeletal work injury has been associated with increased odds of disability one year later.

A cannabinoid is one of a class of diverse chemical compounds that activates the endogenous endocannabinoid system. Exogenous cannabinoids include phytocannabinoids such as tetrahydrocannabinol and cannabidiol, and synthetic cannabinoids such as K2 and 'spice.' *Cannabis* has been cited and recognized as possibly a useful substance for pain management. Indeed, it has been said in the popular press that *cannabis* is safer than opioids and should be used instead of opioids for managing chronic musculoskeletal pain in American football players. However, current evidence suggests that opioids should rarely be prescribed for chronic musculoskeletal pain and many athletes take *cannabis* for chronic musculoskeletal pain management.

Cannabinoids have also been studied for treatment of pain conditions including neuropathic pain, fibromyalgia, spinal cord injury, spasticity from multiple sclerosis, HIV neuropathy and cancer pain. There is evidence that cannabinoids have a modest analgesic effect for some pain conditions such as, for example, refractory neuropathic pain. Cannabinoids are considered possible third-line agents for some chronic pain conditions. Cannabinoids are considered ergolytic, and like opioids, may carry risks, including addiction.

Opioids are a broad group of pain-relieving drugs that work by interacting with opioid receptors in your cells. Opioids can be made from the poppy plant, for example, morphine (Kadian, Ms Contin, others) or synthesized in a laboratory, for example, fentanyl (Actiq, Duragesic, others). What makes opioid medications effective for treating pain can also make them extremely dangerous. When opioid medications travel through human blood and attach to opioid receptors in human brain cells, the cells release signals that muffle the perception of pain and boost feelings of pleasure. Typically, at lower doses, opioids may make one feel sleepy. Yet, higher doses can slow breathing and heart rate, which can lead to death. And the feelings of pleasure that result from taking an opioid can make one want to continue experiencing those feelings, which leads to addiction. Overall, opioid use is prevalent among athletes. Use during a playing career predicts postretirement use. Unfortunately, this issue exists even at the high school level, with similar rates to professional athletes.

Furthermore, para-athletes can experience more pain than their able-bodied counterparts, perhaps because of an increased incidence of injuries in their sports, or the nature of a specific impairment. Although pain or discomfort in para-athletes can be a common clinical feature among those within each of the ten recognized impairment categories, more severe pain may occur in those experiencing stump pain, phantom limb pain, spasticity-related pain or in those who have suffered spinal cord injuries.

Central neuropathic pain is common in athletes following a spinal cord injury or stroke or in those with multiple sclerosis. One study estimated the incidence of neuropathic pain following a spinal cord injury to be 53% for neuropathic pain at the level of the lesion, and 27% for neuropathic pain below the level of the lesion. Phantom limb pain can affect up to 80% of lower limb amputees, and pain in the stump residuum can occur in 55%-76% of these individuals. Chronic musculoskeletal pain is estimated to occur in 60%-80% of individuals with cerebral palsy and reflects increased muscle tone, dystonia and spasticity. The use of pain medications, particularly those used to treat chronic neuropathic pain, is therefore, even higher in para-athletes than in their able-bodied counterparts.

Recognizing the continuing and dire need for effective and safe ways to treat pain, not just for athletes, but the world at large, in ways that do not cause vulnerability to addiction or harm to human organs, the present invention provides an improved approach for formulating compositions that are safe and effective.

SUMMARY

The present method and approach for managing pain safely and effectively overcomes the deficiencies and limitations of prior ways, at least in part by, providing a systematic way to create safe and effective compositions, in which a small dose of active synthetic ingredients is amplified by adding a natural ingredient. This systematic approach provides a way to accomplish a symbiotic relationship between the active synthetic ingredient and the natural ingredient. The positive effects of existing ingredients used in pain-management medications are released, by using a quarter amount in designated levels. Advantageously, using a quarter amount decreases the ill effects caused by use of large amounts of active synthetic ingredients on the human body's organs.

This new approach to creating pain formulation compositions has many benefits. The resulting blended compositions advantageously serve as an anti-inflammatory and decrease addiction vulnerability and dependence, particularly to opioids. The present approach and new formulations reduce side effects compared to current opelousas pain treatment. They are non-intoxicating and non-addictive.

A critical aspect of the present invention amplifies the beneficial results and relief experienced by patients compared to use of existing pain-management medications. The controlled amount of the active synthetic ingredient with a natural ingredient creates a new and improved combination composition that avoids the ill effects that occur with using increased amounts of synthetic active ingredients.

In accordance with one particular composition, a designated amount (0.25 or quarter) of an active synthetic ingredient used to formulate pain-management formulations (as currently approved or prescribed), for example, any one of naproxen, naproxen sodium, acetaminophen, aspirin, and ibuprofen, is combined with a designated amount of cannabidiol ("CBD") isolate. As recognized, CBD isolate is a form of CBD, or cannabidiol, which is a chemical compound present in the *cannabis* plant. Unlike full-spectrum CBD products, CBD isolate does not contain any (or a negligible amount of) tetrahydrocannabinol ("THC"), which is the psychoactive component of *cannabis*.

In some instances, prior to material preparation for formulating these types of new blended compositions, raw materials are obtained and quarantined until a full panel of testing is received and passes a quality and assurance release. A full visual inspection of each ingredient is performed. After the visual inspection of each ingredient, they are batch weighed and prepared for blending.

Another aspect of the present invention blends the new and improved formulations and compositions using a synthetic, an oil or water-based carrier to be an excipient ("carrier"). As known to those skilled in the art, pharmaceutical excipients are substances that are included in a pharmaceutical dosage form not for their direct therapeutic action, but to aid the manufacturing process, to protect, support or enhance stability, or for bioavailability or patient acceptability. The excipient or carrier is prepared in a in a vat and is brought up to temperature levels that range anywhere from about 30° Celsius to 50° Celsius (or 30° Celsius to 80° Celsius). Once the excipient or carrier reaches the required temperature, the CBD isolate in this particular formula (or other cannabinoids used for other formulas) and the active ingredient Naproxen/Naproxen Sodium (acetaminophen, aspirin, or ibuprofen) are then added to the carrier and blended utilizing a High Shear Homogenizer to provide precise and reliable blending. The formula is blended for a designated period of time (e.g., a minimum of ten minutes) or until visual inspection confirms that the active ingredients have become fully suspended/blended into the Carrier. For certain formulations, a flow agent may be added to the mixture. Some examples of flow agents are methylcellulose and magnesium stearate. Once properly suspended, a sample of the blend is obtained for additional testing to confirm potency of the formulation utilizing high-pressure liquid chromatography ("HPLC"). If the potency (or strength) is less or more than what is required, the levels of the ingredients are adjusted and blending is continued until the resulting blend tests to satisfy the appropriate conforming level determined for the batch in preparation. This resulting blend is referred to as the "Formula."

In accordance with another operation and aspect of the present invention, the Formula is subsequently transferred to a "filling" vat, which is attached to a "Drug Enforcement Administration" ("DEA") registered in-line registered liquid encapsulation machine. The fill lines are calibrated to the correct fill volume. For the particular pain-management blended formulation in accordance with the present invention, the fill volume is 0.6 ml. Fill volumes are confirmed through a visual and weight test that is performed. Once everything is properly calibrated, the filling operation may begin by properly dosing the "Formula" into vegetarian capsules. The capsules may then be capped and sealed with Hydroxypro Methylcellulose E6. The in-line system used may be configured to eject the capsules into sterile bins, which are transferred into drying racks for proper curing of the sealant and to enable visual inspection for any leaks or defects. The final capsules that pass this step may be designated as the "Formulated Capsules."

In accordance with the formulation procedure of creating new combination or blended compositions in accordance with the present invention, a "post-encapsulation" operation follows. After a full curing, samples of the formulated capsules are randomly selected for further testing of potency and weight to confirm accuracy. Once confirmed, the batch may be released from quarantine and preparation for packaging into the final closure system may start.

In accordance with yet another aspect, formulated capsules may be packaged into suitable bottles, for example, 12 cc White HDPE/PET bottles with child resistant liners and lids. Once the packaging is complete, samples may be obtained for stability testing as well as performing immediate tests for potency and microbial contaminants.

BRIEF DESCRIPTION OF THE DRAWINGS

The present invention is illustrated by way of example, and not by way of limitation in the figures of the accompanying drawings in which like reference numerals are used to refer to the same or similar elements.

DETAILED DESCRIPTION

Figure 1:
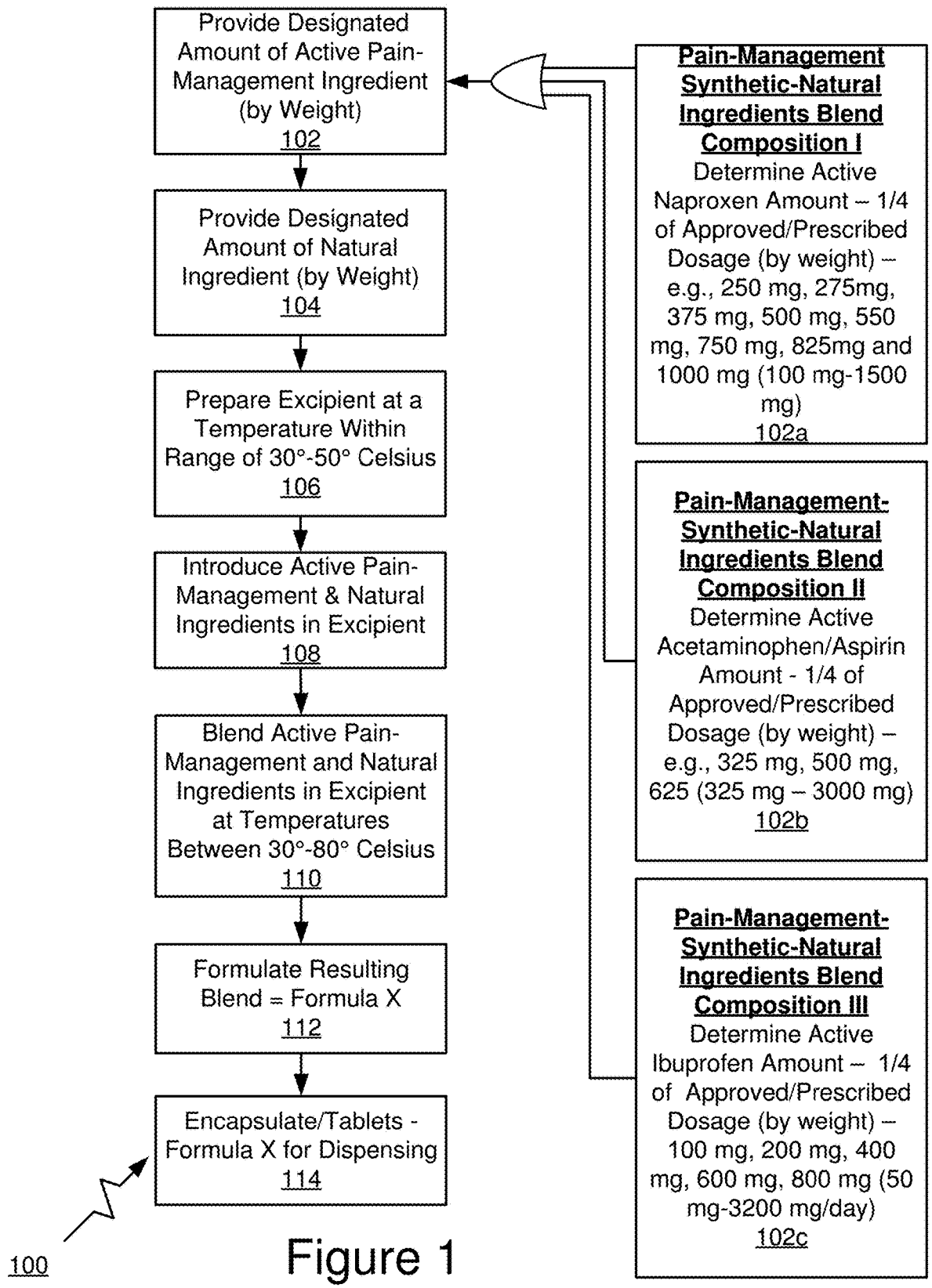
FIG. 1 is a flow chart illustrating a new and improved approach to creating new pain-management formulations and compositions ("pain-management synthetic-natural ingredients blend composition I," "pain-management synthetic-natural ingredients blend composition II," and "pain-management synthetic-natural ingredients blend composition III,") designed to amplify the beneficial advantages of a small amount (0.25 or quarter) of active synthetic ingredients currently prescribed with natural ingredients to avoid the ill effects of these active synthetic ingredients.

This disclosure provides new and improved systems and methods for amplifying the beneficial effects and advantages of a quarter (0.25) amount of active synthetic ingredients in current pain-management prescribed medications. This disclosure also describes how to produce new and improved pain-management compositions and formulations that improve the effects of small amounts of pain-management medications without increasing the potency of their active ingredients.

In accordance with one embodiment, the present invention introduces a designated amount of a natural ingredient into a blend with a quarter amount (0.25) of synthetic active ingredient (naproxen, naproxen sodium, aspirin, acetaminophen, or ibuprofen) to create a new and improved composition that amplifies the effects of the active synthetic ingredient, while preventing the adverse effects caused by increased medication potency on a human body's organs. It will be recognized by those skilled in the art that formulation refers to the "act or process of formulating any mixture or substance prepared according to a particular formula."

Techniques and compositions for delivery of pharmaceutical formulations or compositions, including oral delivery, are well known. However, it will be recognized that formulation of compositions for delivery, particularly oral delivery poses challenges. One challenge is to produce an oral controlled-release dosage composition that provides a favorable reaction in a human, by recreating a symbiotic relationship of an active ingredient with other natural ingredients designed to balance the ill affects active ingredients at high potency levels. The best compositions must accomplish administering a relatively steady dose of active ingredient over the approximately eight hours during which the dosage composition passes through the gastrointestinal tract. Sustained release is often achieved by providing the composition with a coating that delays release, or by formulating the composition in a tablet in such a way that it disintegrates relatively slowly, releasing the active ingredient as it releases.

It will also be recognized by those skilled in the art that a tablet, however, once ingested, is subject to considerable mechanical and chemical stresses as it passes through the esophagus, stomach, duodenum, jejunum, ileum, large intestine and colon, thus providing a significant challenge in maintaining controlled release of the active ingredient in the formulation. Acids, enzymes and peristalsis can cause the tablet to break apart, resulting in exposure of the inside of the tablet and an increase in surface area of the tablet material. This will tend to increase the delivery rate of the active ingredient or otherwise adversely affect the controlled release properties of the dosage form.

Another challenge, is to produce a dosage form of the active synthetic ingredient, including an oral dosage form, that reduces the potential for drug abuse.

In accordance with one embodiment of the present invention, some new oral blended compositions are formulated including a ratio of a designated quarter (0.25) amount of an active synthetic ingredient in current prescribed doses of pain-management medications to a designated amount of a natural ingredient to formulate a blend that is effective yet safe. The new and improved compositions use existing pain-management medications such as naproxen, naproxen sodium, acetaminophen, aspirin, and ibuprofen in small amounts or low doses (0.25) and the effects of these small amounts are amplified by a designated amount of a CBD isolate. The active synthetic ingredient and the natural ingredient are effective because of the symbiotic relationship between the two ingredients.

In accordance with some embodiments, the present invention provides methods for producing blended formulations, compositions, or formulas that reduce the ill effects of active ingredients in medications that adversely affect human organs.

In one blended composition of the present invention described here, naproxen is blended with a CBD isolate. As in recognized by those skilled in the art, Naproxen is commonly used by many as a pain medication that relieves inflammation and joint stiffness. A person may take naproxen to address myriad health reasons, including but not limited to, rheumatoid arthritis, osteoarthritis, and dental pain. Other NSAIDs in the same medication class include acetylsalicylic acid, diclofenac, ibuprofen, and meloxicam. It is recognized that naproxen works by blocking the enzyme that produces prostaglandins. Prostaglandins play an essential role in inflammation. The body produces them at the site of injured tissue, and they cause redness, heat, swelling, and pain.

As recognized by those skilled in the art, naproxen is available as naproxen or naproxen sodium. The major difference between naproxen and naproxen sodium is that naproxen sodium is more rapidly absorbed. A human body may absorb peak levels of naproxen in two to four hours and naproxen sodium in one to two hours. In other words, a human body absorbs naproxen sodium faster than regular naproxen. Before drugs can be clinically effective, they must be absorbed. Absorption is the process of a drug moving from its site of delivery into the bloodstream. The chemical composition of a drug or medication, as well as the environment into which a drug or medication is placed, work together to determine the rate and extent of drug absorption.

Typically, people use naproxen to address myriad conditions, including but not limited to rheumatoid arthritis, osteoarthritis, ankylosing spondylitis, juvenile arthritis, tendonitis, bursitis, gout attacks, muscle aches, strains, sprains, headaches, dental pain, and fever. In the United States, over-the-counter ("OTC") naproxen is called "Aleve." Prescription naproxen is known as "Naprosyn" and "Anaprox." It is recognized by those skilled in the art that there are various types and strengths of naproxen. Regular naproxen tablets contain 250 milligrams ("mg") 375 mg, or 500 mg of naproxen. Higher doses include 550 mg, 750 mg, 825 mg, and 1000 mg. Fast-absorbing naproxen sodium is available in 220 mg OTC capsules and tablets, and 275 mg and 550 mg tablets by prescription. A higher dose of 750 mg is also available. Low-dose naproxen is available in tablet or capsule form. Naproxen also exists in suspension form containing 25 mg of the drug per milliliter ("ml").

The active ingredients in naproxen are microcrystalline cellulose, croscarmellose sodium, povidone, magnesium stearate, and iron oxide. The active ingredients of naproxen sodium are microcrystalline cellulose, croscarmellose sodium, povidone, magnesium stearate, colloidal silicon dioxide, and talc. Naproxen suspension contains methylparaben, fumaric acid, magnesium aluminum silicate, sodium chloride, sorbitol solution (70%), sucrose, and flavor and FD&C Yellow No. 6. Naproxen is also available in enteric-coated tablets. These tablets release naproxen in the intestine rather than in the stomach. This formulation helps prevent gastrointestinal side effects that manufacturers have sometimes associated with naproxen. Similar to regular naproxen, enteric-coated tablets come in tablets of 250 mg, 375 mg, and 500 mg.

For all forms of naproxen, medical advice is to take naproxen at the lowest effective dose for the shortest duration to prevent side effects. For fever and mild to moderate pain, adults between twelve and sixty-five years old are typically advised to take one 220 mg tablet of naproxen every twelve hours. For osteoarthritis, rheumatoid arthritis, and ankylosing spondylitis, people manage the symptoms with a dose of 220 mg to 550 mg of naproxen every twelve hours. Clearly, naproxen does not cure these conditions but offers relief from pain and inflammation. Nonetheless, people experiencing acute gout attacks may take 825 mg for one dose, followed by 275 mg every eight hours. For juvenile rheumatoid arthritis, doctors can prescribe naproxen to manage the pain and inflammation caused by juvenile rheumatoid arthritis. It is common to use naproxen to relieve pain from headaches and migraine headaches. People may take 550 mg of naproxen sodium every twelve hours and may increase it to 825 mg if needed. The daily dose should not exceed 1,375 mg. Naproxen sodium is degraded more slowly than regular naproxen and other NSAIDs. This means that naproxen sodium should remain active for longer than other anti-inflammatory drugs. In some instances, after two hours, headache pain relief is lower with naproxen sodium than with other NSAIDs. It is recognized that although naproxen can be used to reduce the pain of headaches and migraine headaches, other NSAIDs may provide better relief. People use over the counter naproxen for a short-term period of between three to five days for pain and no more than three days for fever. If they need ongoing treatment, people typically consult their doctor first. For severe pain, studies have not shown any benefit in using daily doses higher than 1000 mg, but some sources suggest a maximum of 1650 mg per day for up to six months for arthritis. Increased doses are risky not only in the short term as common side effects of naproxen may include headache and dizziness, but also in the long term. The frequency and severity of side effects that naproxen causes depend on several factors. Considerations include the dose and duration of treatment, other medical diagnoses a person may have, and individual risk factors. In all the example scenarios described above, it is clear that consistent use of larger doses can adversely affects the human body.

There are many common and serious side effects of naproxen that may occur in three to nine percent of people. In the gastrointestinal tract, people can experience heartburn, constipation, abdominal pain, and nausea. In the central nervous system, people can experience headache, dizziness, drowsiness, depression, and fatigue. Use of naproxen can result in itchy skin, ecchymoses, and skin eruptions. The cardiovascular system can experience dyspnea and peripheral edema. Some experience ringing in the ear. Further, although people can buy low-dose naproxen without a prescription, it is not safe for everyone. People with serious heart conditions, such as heart disease, cerebrovascular disease, and congestive heart failure, may experience severe side effects from taking naproxen, for example, heart attack, stroke, and blood clots. People with high blood pressure only take naproxen cautiously. Naproxen can cause sodium retention in the kidneys, which can result in increased blood pressure. A person with high blood pressure should consult their doctor before taking naproxen. For some, gastrointestinal side effects of taking naproxen can be severe. Bleeding in the stomach, the formation of ulcers, and stomach or intestinal blockages can occur when taking naproxen. Most often, older adults are the most vulnerable age group for gastrointestinal side effects. People who have a history of ulcers or gastrointestinal bleeding have a ten-fold higher risk for developing a bleed when taking naproxen. For these individuals, even short-term treatment can be risky.

Further, naproxen may interact with several prescription and nonprescription drugs. Drinking alcohol and taking naproxen may increase the risk of gastrointestinal side effects. Also, people taking the antidepressant class of selective serotonin reuptake inhibitors ("SSRIs") have an increased of gastrointestinal bleeding and ulcers when taking naproxen. As is well known to those skilled in the art, SSRIs include citalopram, escitalopram, fluoxetine, fluvoxamine, paroxetine, sertraline, and vortioxetine. Oral steroids, such as prednisone and antiplatelet drugs, may also increase stomach and intestinal bleeding and ulceration if people combine them with naproxen. Naproxen blocks the aggregation of platelets, which is an essential step in blood clotting. Blocking the aggregation of platelets can increase the time it takes for bleeding to stop. Combining naproxen with blood thinners, such as antiplatelet and anticoagulant medications, must be monitored by medical professionals. If a person has a history of an allergy or intolerance to any NSAID, they are advised to not take naproxen. Cross-allergies and intolerances may occur between NSAIDs. One type of intolerance to NSAIDs is aspirin-induced asthma. Asthma symptoms and severe allergic reactions may occur when affected individuals take aspirin. These people are advised to avoid naproxen and all other NSAIDs because of the risk of developing even more severe side effects. People are advised to not combine certain antidepressants, high blood pressure, and blood thinners with naproxen. Certain diagnoses may increase the likelihood of experiencing side effects, such as heart disease, ulcers, and kidney disease.

Naproxen is a prescription and nonprescription NSAID. People may use it to relieve pain that inflammation causes. Naproxen is not safe for everyone. People taking certain medications are advised to use naproxen cautiously to avoid side effects. For example, people with stomach or intestinal diseases, cardiac disease, or kidney disease are advised to discuss the use of NSAIDs with their doctor. Only at the appropriate dose or level is naproxen considered a safe and effective pain reliever. Accordingly, the new approach of the present invention to enhance and amplify the effects of a smaller and safe amount of naproxen by adding a natural ingredient to it is beneficial.

Referring now to FIG. 1, the method 100 produces new and improved pain-management blended formulations and compositions that are effective yet safe. The new approach to pain management provides an active synthetic ingredient (at currently utilized levels) in a designated amount (a quarter or 0.25) by weight of active ingredients in prescribed doses, as is designated by block 102. As illustrated in block 102a, a "pain-management synthetic-natural ingredients blend composition I" is formulated by determining an active naproxen amount, and taking a quarter or 0.25 of active ingredient in prescribed doses. The prescribed doses may range anywhere from 100 mg to 1500 mg. Typical prescribed doses are 250 mg, 275 mg, 375 mg, 500 mg, 550 mg, 750 mg, 825 mg, and 1000 mg.

As illustrated in block 102b, a "pain-management synthetic-natural ingredients blend composition II" is formulated by determining an active acetaminophen/aspirin in a designated amount (a quarter or 0.25) by weight of active ingredients in prescribed doses. The prescribed doses may be 325 mg, 500 mg, 625 mg. The range may be anywhere from 325 mg to 3000 mg.

As illustrated in block 102c, a "pain-management synthetic-natural ingredients blend composition III" is formulated by determining an active ingredient in ibuprofen in a designated amount (a quarter or 0.25) by weight of active ingredients in prescribed doses. The prescribed doses may be 100 mg, 200 mg, 400 mg, 600 mg, and 800 mg. The range may be anywhere from 50 mg to 3200 mg.

The pain-management active ingredient may be an opioid-related synthetic ingredient, for example, one from a group of: Oxycodone, Hydrocodone-Acetaminophen, Hydrocodone bitartrate, Hydrocodone-Homatropine, Hydrocodone-Ibuprofen, Pseudoephedrine-Hydrocodone, Hydrocodone-Chlorpheniramine, Hydrocodone-Chlorpheniramine-Pseudoephedrine, Morphine, Morphine-Naltrexone, Hydromorphone, Fentanyl Citrate, Fentanyl, Codeine Polistirex-Chlorpheniramine Polistirex/CBD Isolate Composition, Acetaminophen and Codeine Phosphate, Methadone, Oxymorphone, Meperidine, Carfentanil, and Buprenorphine. The designated amount for an opioid blend composition should only use 0.25 or a quarter amount of approved prescribed levels of any of the opioids identified. The maximum amount by weight should not exceed 288 mg, although normal doses are 9-12 mg every twelve hours.

The method 100 also provides a natural ingredient in a designated amount by weight as designated by block 104 in the flow chart. The method 100 requires preparing an excipient at a temperature within a range of about 30-50 degrees Celsius as illustrated by block 106. The method 100 proceeds to introducing the active pain-management and natural ingredients in the designated amounts by weight in the Excipient as designated by block 108. The method 100 proceeds to the next block 110, including operations for blending the active ingredient (some active ingredients) and the natural ingredient in the Excipient at a temperature that falls within a range of between 30-80 degrees Celsius (by the heating the Excipient above 50 degrees Celsius if required). In some embodiments, for some active ingredients, the Excipient may remain at a temperature within a range of about 30-50 degrees Celsius (requiring no heating). In some embodiments, for some active ingredients, the blending process may require the Excipient to be slightly heated to a temperature that falls within a range of 30-60 degrees Celsius. The blending process yields a formula as designated by block 112. The formula is encapsulated for dispensing as illustrated by block 114. In some embodiments, the formula may be provided as formulated tablets.

In one embodiment, the present invention provides compositions that are encapsulated for oral use to relieve pain in athletes and others. An individual capsule is formulated in solid form with the drug formulations (blended compositions) provided inside the capsule as a liquid oil or in powder form. The drug formulation comprises at least an active drug ingredient, a CBD isolate, which is a natural ingredient, and a natural USP grade carrier oil. In a specific formulation, the active drug ingredient is naproxen, which is a synthetic drug. In other embodiments, the present invention provides a composition with other active ingredients and a CBD isolate, and a natural USP grade carrier oil. In one embodiment, the composition has 0.25 or quarter amount of the active ingredient in typical approved or prescribed doses of naproxen and 200 mg of the CBD isolate. In another embodiment, the CBD isolate/formulation may be anywhere between 100 mg to 500 mg. It should be recognized by those skilled in the art that the potency levels of the CBD isolate are greater than 98.5% CBD (>98.5% CBD<0.09% Δ9-THC)

Variable concentrations of the active ingredients may be used. In some embodiments, the carrier oil may be hemp seed oil, olive oil, grapeseed oil, sesame oil, or MCT (medium-chain triglycerides) oil. In other embodiments the excipient may be polyethylene glycol or polysorbate 80/60/100. In some embodiments, additional added ingredients may be added, for example, between 0.001% and 20%. The additional ingredients may be any one of: 5-HTP (5-hydroxytryptophan), L-Theanine, Melatonin, Vitamin B6, Zinc, Magnesium (Glycinate, biglycinate, or oxide), Jujube seed powder, Ashwagandha, Phosphatidyle Serine, Phospholipids, Huperzine, Lecithin, Willow Bark extract (Salacin), Ginsenosides, Bacopa, Gingko Biloba, Cannabinoids (Cannabinol (CBN), Cannabidiolic Acid (CBDa), Cannabigerol (CBG), Cannabigerolic Acid (CBGa), Tetrahydrocannabinolic Acid (CBC), and Terpenes (Myrcene, Limonene, Beta Caryophyllene, Linalool, B-Pinene, Camphene, Eucalyptol, Humulene, and Geraniol).

Figure 2A:
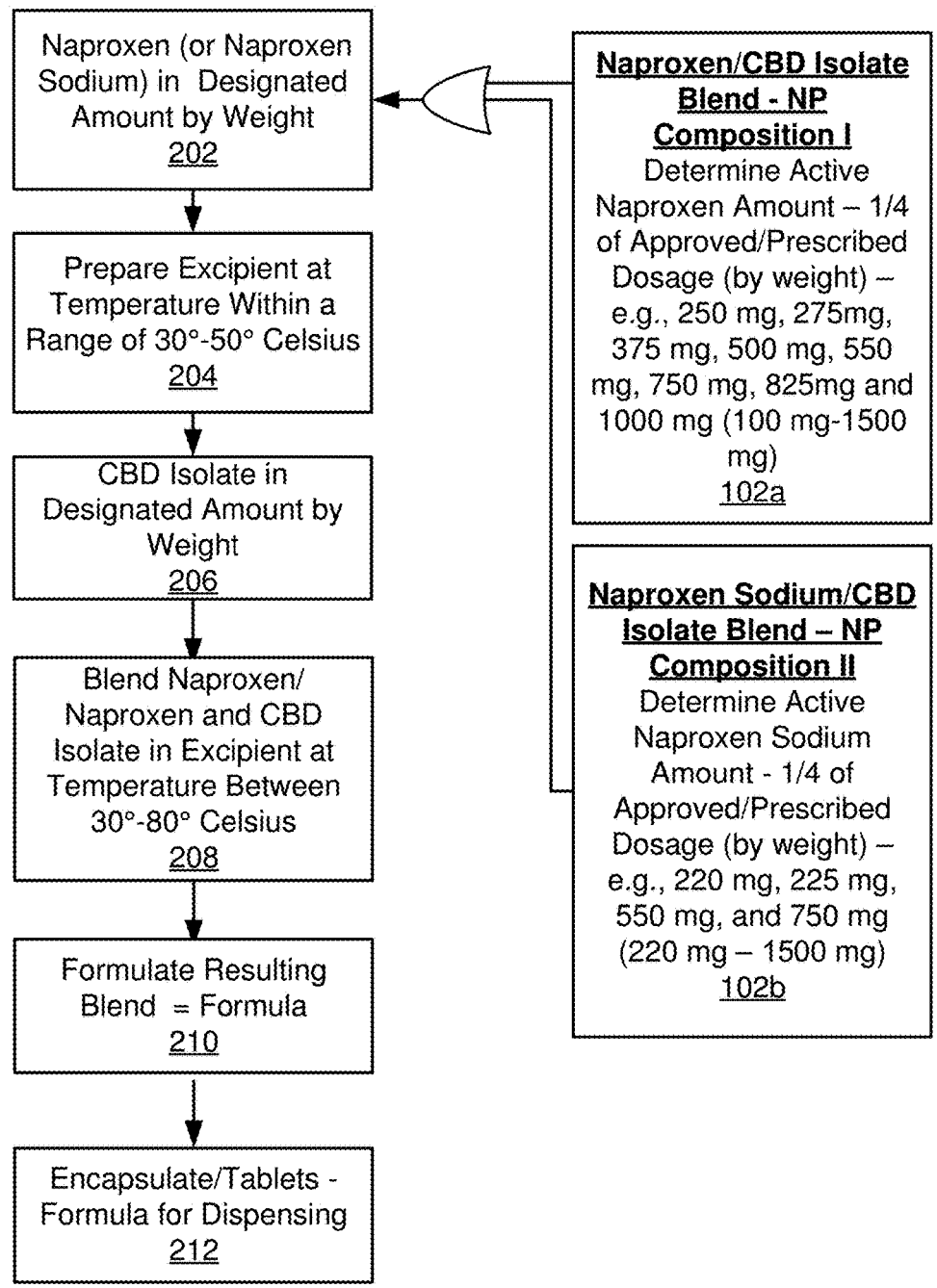
FIG. 2A is a flow chart illustrating a new and improved method to create blended compositions of a quarter (0.25) amount of naproxen and naproxen sodium in current prescribed levels with CBD isolate ("NP Composition I" and "NP Composition II").

Referring now to FIG. 2A, the method 200A in accordance with a specific example provides a process indicated in block 202 for providing naproxen/naproxen sodium in a designated amount by weight. The method 200A proceeds to the next operation, which requires preparing the excipient at a temperature that falls within a range of 30-50 degrees Celsius, as indicated by block 204. The method 200A proceeds to the next operation, which requires adding or introducing a CBD Isolate in a designated amount by weight as illustrated by block 206. The method 200A proceeds to the next operation, which requires blending the active ingredient and the CBD Isolate in the Excipient at a temperature between 30-80 degrees Celsius (by heating above 50 degrees Celsius if required) as illustrated by block 208. In some embodiments, for some active ingredients, the Excipient may remain at a temperature within a range of about 30-50 degrees Celsius (requiring no heating). In some embodiments, for some active ingredients, the blending process may require the Excipient to be slightly heated to a temperature that falls within a range of 30-60 degrees Celsius.

The blending yields a resulting blend or "Formula" as illustrated by block 210. The method 200A in one embodiment proceeds to the next operation, which requires encapsulation of the Formula for dispensing, as designated by block 212. As will be recognized by those skilled in the art, the new and improved blended composition may be formulated with different portions with at least 25% active ingredient amounts of approved or prescribed dosages with 100 mg to 400 mg (or 100 mg to 500 mg) of CBD isolate. Other inactive ingredients or fillers may be added as desired.

TABLE 1

Naproxen

| Medication | Active Ingredient Amount of Dosage | CBD Isolate Amount | Inactive Ingredients (Additives/ Fillers) | Composition |
| --- | --- | --- | --- | --- |
| Naproxen | 25% | 100 mg-400 mg | 55%-99% | Example Composition I |

Figure 2B:
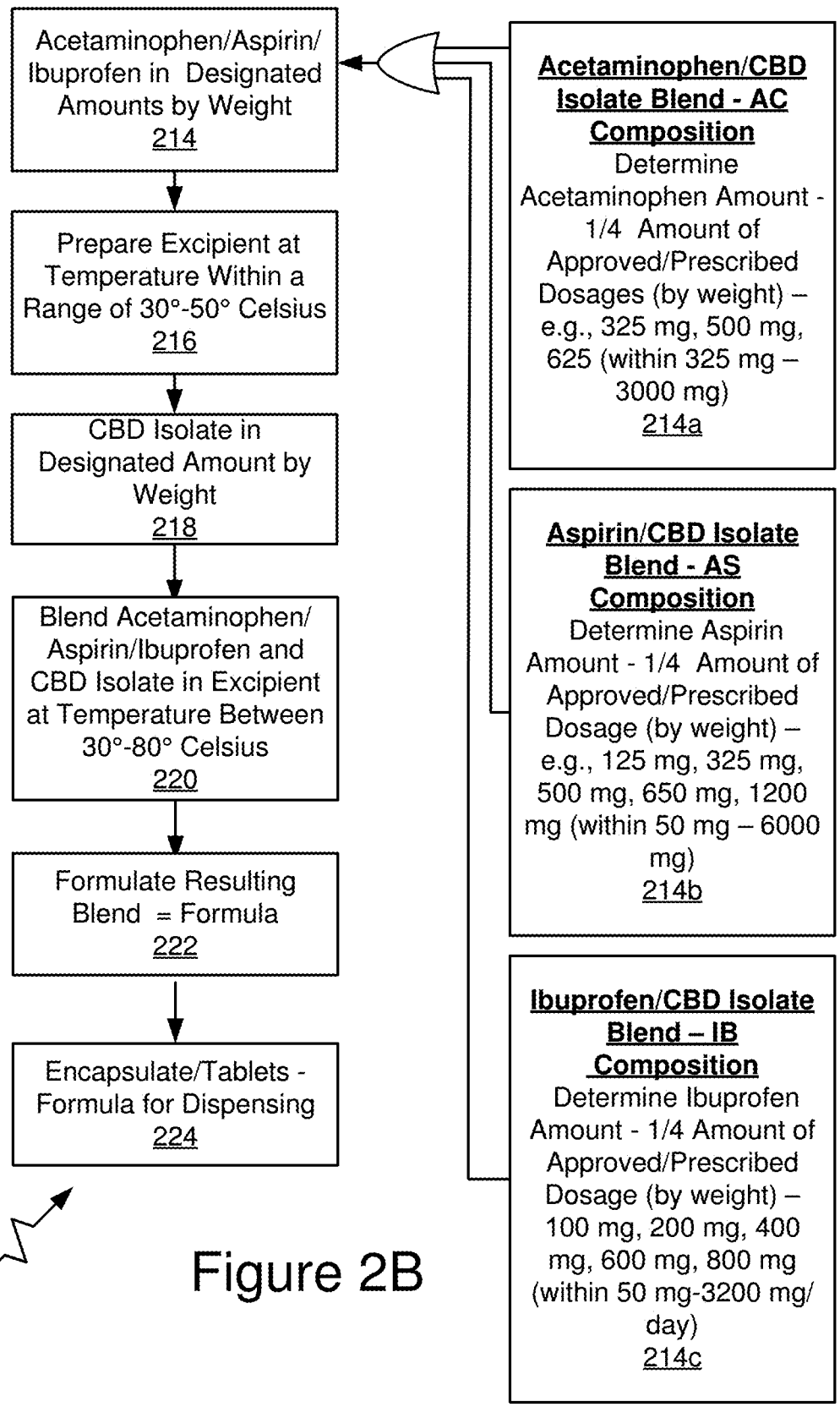
FIG. 2B is a flow chart illustrating a new and improved method to create blended composition of a quarter (0.25) amount of acetaminophen, aspirin, or ibuprofen in current prescribed levels with CBD isolate ("AC Composition," "AS Composition," "IB Composition," respectively).

Referring now to FIG. 2B, the method 200B in accordance with a specific example provides one of acetaminophen, aspirin, and ibuprofen and blends it with CBD isolate in a designated amount (quarter or 0.25) by weight as illustrated by block 214. To formulate a pain-management composition with acetaminophen, as illustrated by block 214a, a quarter or 0.25 of approved or prescribed dosage amounts is determined and used. The quarter or 0.25 amount is of 325 mg-3000 mg, where standard doses are either 325 mg, 500 mg, or 625 mg. In accordance with another embodiment, to formulate a pain-management composition with aspirin, as illustrated by block 214b, a quarter or 0.25 of prescribed dosage amounts is determined and used. The quarter or 0.25 mg is of 50 mg-6000 mg, where typical prescribed doses are 125 mg, 325 mg, 500 mg, 650 mg, and 1200 mg. In accordance with yet another embodiment, to formulate a pain-management composition with ibuprofen, as illustrated by block 214c, a quarter or 0.25 of prescribed dosage amounts is determined and used. The quarter or 0.25 mg is of 50 mg-3200 mg, where typical prescribed doses are 100 mg, 200 mg, 400 mg, 600 mg, and 800 mg.

The method 200B requires preparing the Excipient at a temperature within a range of 30-50 degrees Celsius, as indicated by block 216. The method 200B proceeds to the next operation illustrated by block 218, which requires adding or introducing a CBD Isolate in a designated amount by weight (100 mg-400 mg or 100 mg-500 mg). The method 200B proceeds to the next block 220 of operations, which require blending the acetaminophen/aspirin/ibuprofen and the CBD Isolate in the Excipient at a temperature between 30-80 degrees Celsius. In some embodiments, for some active ingredients, the Excipient may remain at a temperature within a range of about 30-50 degrees Celsius (requiring no heating). In some embodiments, for some active ingredients, the blending process may require the Excipient to be slightly heated to a temperature that falls within a range of 30-60 degrees Celsius. The blending yields a blend or "Formula" as illustrated by block 220. The method 200B in one embodiment requires encapsulation of the Formula for dispensing, as designated by block 224. As will be recognized by those skilled in the art, the new and improved blended composition may be formulated with different portions with at least 25% active ingredient amounts of prescribed dosages with 100 mg to 400 mg of CBD isolate. Other inactive ingredients or fillers may be added as desired.

Typical fillers for tablets and capsules (e.g., powder) may include starch, calcium salts, and sugars like lactose. In liquid formulations, materials like glycerin and water are used to dissolve (or suspend) active ingredients and simplify dose measurements. Alcohol, a historically popular diluent, now rarely used, should be avoided. In some embodiments, minimal amounts of preservatives may be added to the compositions, including at least one from a group of: Povidone, Tocopherol (Vitamin E), BHA (butylatedhydroxyanisole), BHT (butylatedhydroxytoulene), propyl gallate, citric acid, methyl paraben, ethyl paraben, propyl paraben, butyl paraben, benzyl alcohol, chlorobutanol, phenol, meta cresol, chloro cresol, benzoic acid, sorbic acid, thiomersal, phenylmecuric nitrate, bronopol, propylene glycol, benzylkonium chloride, and benzethonium chloride. It will be recognized by those skilled in the art that these preservatives are used in manufacture of pharmaceutical products. In some instances, different concentration levels are used in oral liquids, parenterals, ophthalmic/nasal, and ointments and creams.

TABLE 2

Acetaminophen and Aspirin

| Medication | Active Ingredient Amount of Dosage | CBD Isolate Amount | Inactive Ingredients (Additives/ Fillers) | Composition |
| --- | --- | --- | --- | --- |
| Acetaminophen | 25% | 100 mg-400 mg | 55%-99% | AC Composition |
| Aspirin | 25% | 100 mg-400 mg | 55%-99% | AS Composition |
| Ibuprofen | 25% | 100 mg-400 mg | 55%-99% | IB Composition |

Other pain-management active ingredients, for example, Opioids are also used to create the improved compositions and formulations. As described and illustrated in Table 3 (below), 0.25 or 25% of the active ingredient in an opioid is used and blended with a CBD isolate to create improved and effective compositions. Other inactive ingredients or fillers may be added as desired. The improved compositions created include:

1) Oxycodone/CBD Isolate Blend Composition
2) Hydrocodone-Acetaminophen/CBD Isolate Composition
3) Hydrocodone bitartrate/CBD Isolate Composition
4) Hydrocodone-Homatropine/CBD Isolate Composition
5) Hydrocodone-Ibuprofen/CBD Isolate Composition
6) Pseudoephedrine-Hydrocodone/CBD Isolate Composition
7) Hydrocodone-Chlorpheniramine/CBD Isolate Composition
8) Hydrocodone-Chlorpheniramine-Pseudoephedrine/CBD Isolate Composition
9) Morphine/CBD Isolate Composition
10) Morphine-Naltrexone/CBD Isolate Composition
11) Hydromorphone/CBD Isolate Composition
12) Fentanyl Citrate/CBD Isolate Composition
13) Fentanyl/CBD Isolate Composition
14) Codeine Polistirex-Chlorpheniramine Polistirex/CBD Isolate Composition
15) Acetaminophen and Codeine Phosphate
16) Methadone
17) Oxymorphone
18) Meperidine
19) Carfentanil
20) Buprenorphine

TABLE 3

| Pain Medications (Opioids) | | | | |
|---|---|---|---|---|
| Pain Medication | Active Ingredient Amount of Dosage | CBD Isolate Amount | Inactive Ingredients (Additives/Fillers) | Composition |
| Oxycodone | 25% | 100 mg-400 mg | 55%-99% | Oxycodone/CBD Isolate Blend Composition |
| Hydrocodone-Acetaminophen | 25% | 100 mg-400 mg | 55%-99% | Hydrocodone-Acetaminophen/CBD Isolate Composition |
| Hydrocodone bitartrate | 25% | 100 mg-400 mg | 55%-99% | Hydrocodone bitartrate/CBD Isolate Composition |
| Hydrocodone-Homatropine | 25% | 100 mg-400 mg | 55%-99% | Hydrocodone-Homatropine/CBD Isolate Composition |
| Hydrocodone-Ibuprofen | 25% | 100 mg-400 mg | 55%-99% | Hydrocodone-Ibuprofen/CBD Isolate Composition |
| Pseudoephedrine-Hydrocodone | 25% | 100 mg-400 mg | 55%-99% | Pseudoephedrine-Hydrocodone/CBD Isolate Composition |
| Hydrocodone-Chlorpheniramine | 25% | 100 mg-400 mg | 55%-99% | Hydrocodone-Chlorpheniramine/CBD Isolate Composition |
| Hydrocodone-Chlorpheniramine-Pseudoephedrine | 25% | 100 mg-400 mg | 55%-99% | Hydrocodone-Chlorpheniramine-Pseudoephedrine/CBD Isolate Composition |
| Morphine | 25% | 100 mg-400 mg | 55%-99% | Morphine/CBD Isolate Composition |
| Morphine-Naltrexone | 25% | 100 mg-400 mg | 55%-99% | Morphine-Naltrexone/CBD Isolate Composition |
| Hydromorphone | 25% | 100 mg-400 mg | 55%-99% | Hydromorphone/CBD Isolate Composition |
| Fentanyl Citrate | 25% | 100 mg-400 mg | 55%-99% | Fentanyl Citrate/CBD Isolate Composition |
| Fentanyl | 25% | 100 mg-400 mg | 55%-99% | Fentanyl/CBD Isolate Composition |
| Codeine Polistirex-Chlorpheniramine Polistirex | 25% | 100 mg-400 mg | 55%-99% | Codeine Polistirex-Chlorpheniramine Polistirex/CBD Isolate Composition |
| Acetaminophen and Codeine Phosphate | 25% | 100 mg-400 mg | 55%-99% | Acetaminophen and Codeine Phosphate/CBD Isolate Composition |
| Methadone | 25% | 100 mg-400 mg | 55%-99% | Methadone/CBD Isolate Composition |
| Oxymorphone | 25% | 100 mg-400 mg | 55%-99% | Oxymorphone/CBD Isolate Composition |
| Meperidine | 25% | 100 mg-400 mg | 55%-99% | Meperidine/CBD Isolate Composition |
| Carfentanil | 25% | 100 mg-400 mg | 55%-99% | Carfentanil/CBD Isolate Composition |
| Buprenorphine | 25% | 100 mg-400 mg | 55%-99% | Buprenorphine/CBD Isolate Composition |

Figure 3:
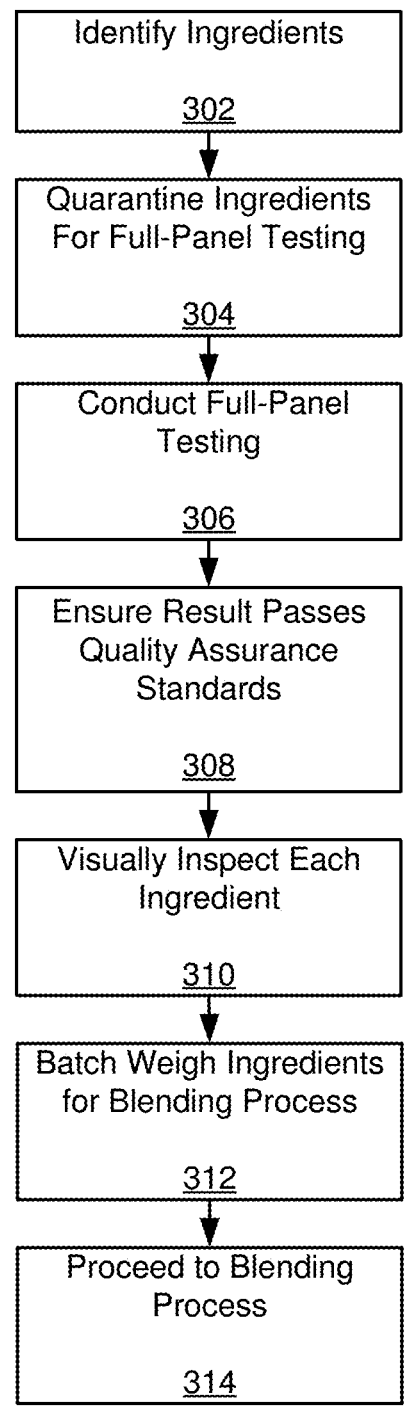
FIG. 3 is a flow chart of the method steps before blending of the ingredients.
Figure 3:
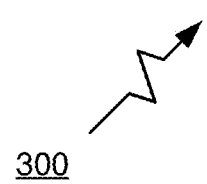

Referring now to FIG. 3, in accordance with yet another embodiment, the method 300 begins with identifying ingredients as indicated by block 302. The process of making the specific formulations and compositions in accordance with the present invention involves obtaining the "raw" materials used for creating them. It will be recognized by those skilled in the art that "raw materials" in this example are "input" substances used in both chemical synthesis and processing and include any buffers, cleaning agents, common solvents and commonly used synthetic starting materials such as amino acids. When these materials are delivered, they must be tested to confirm that they are indeed what they claim to be and have not been inappropriately labelled. The method 300 proceeds to the next operation, which requires quarantining the ingredients for performing a "full-panel" testing as illustrated by block 304. The method 300 proceeds to the next operation, which requires the "full panel" testing as illustrated by block 306. The method 300 proceeds to the next operation, which requires a process to ensure that the results pass quality assurance standards as illustrated by block 308. The method 300 subsequently proceeds to the next operation, which requires visually inspecting each ingredient as illustrated by block 310. The method 300 proceeds to the next operation, which requires weighing ingredients by batches and preparing for blending as illustrated by block 312, after which the method 300 proceeds to the blending process, as illustrated by block 314. After a visual inspection of each ingredient indicated above, they are weighed for each batch and prepared for blending to formulate the required composition. Automated dispensing systems may be utilized for the transfer and weighing of excipients, active pharmaceutical ingredients ("API's") and lubricants into a variety of containers and processes. The use of screw feeders in both loss-in-weight ("LIW") and gain-in-weight ("GIW") dispensing systems ensure the accurate metering of the product to the process or container.

Figure 4A:
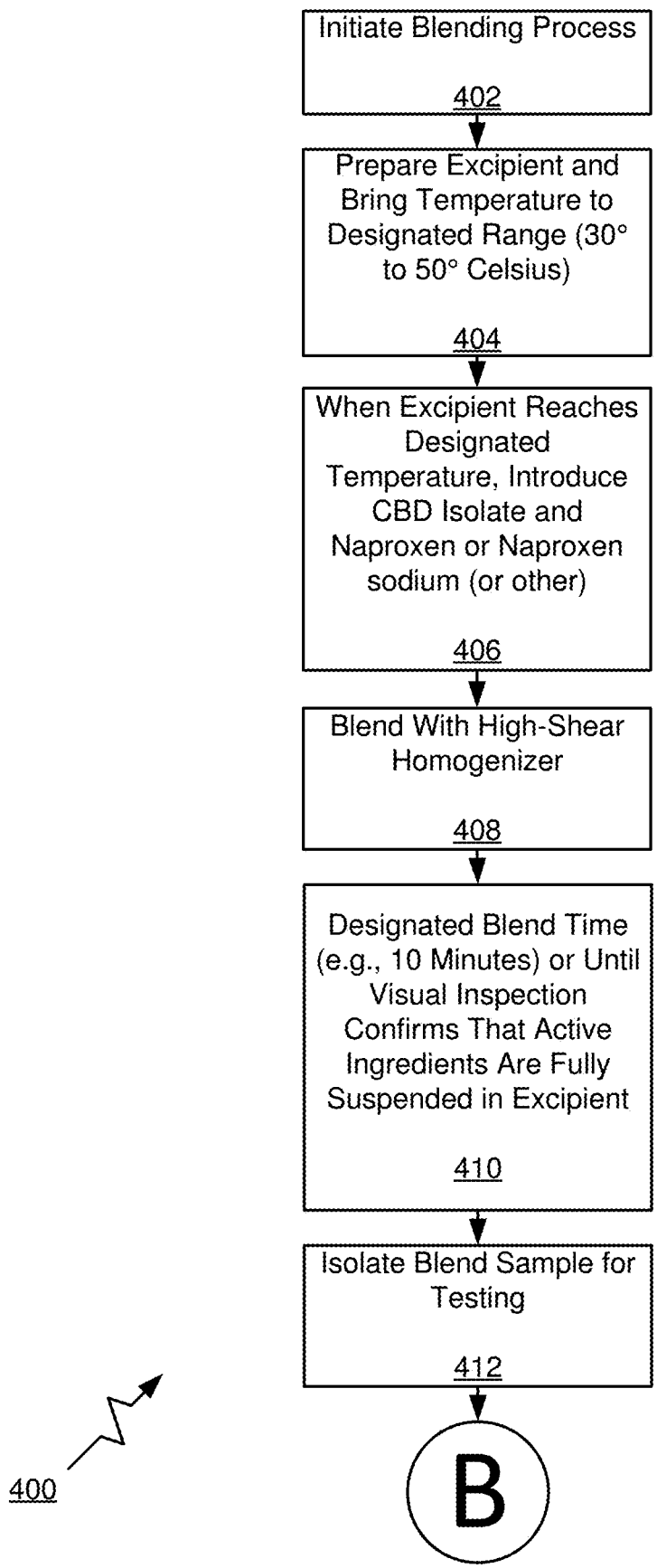
FIG. 4A is a flow chart illustrating the blending process by which the new and improved compositions are formulated.

Referring now to FIG. 4A, the method 400 directed to the process of formulating compositions initiates the blending process as indicated by block 402. The method 400 proceeds to the next operation, which involves preparing the excipient or carrier ("Excipient") and bringing its temperature to a designated range, somewhere within 30 to 50 degrees Celsius. This process is illustrated by block 404. As further illustrated by block 406, when the Excipient reaches a designated temperature, the CBD isolate and the naproxen/naproxen sodium (or other active ingredient, for example, Acetaminophen, Aspirin, ibuprofen or other) is introduced into the carrier. This process is illustrated by block 406. The blending is performed by using a High-Shear Homogenizer as illustrated by block 408. It is critical to have the active ingredients evenly dispersed so that active ingredient percentage remains constant for any quantity measured. It should be understood that the same approach may be applied to other active ingredients, using other variations of natural ingredients. In some instances, the designated blending time may be about ten minutes. In other instances, it may take less or more time. The blending should be continued until a visual inspection confirms that the active ingredients are fully suspended in the Excipient. This process is illustrated by block 410. As further illustrated by block 412, a sample may be obtained for testing. The method 400 continues via connector "B" to the next block of operations illustrated in FIG. 4B.

Figure 4B:
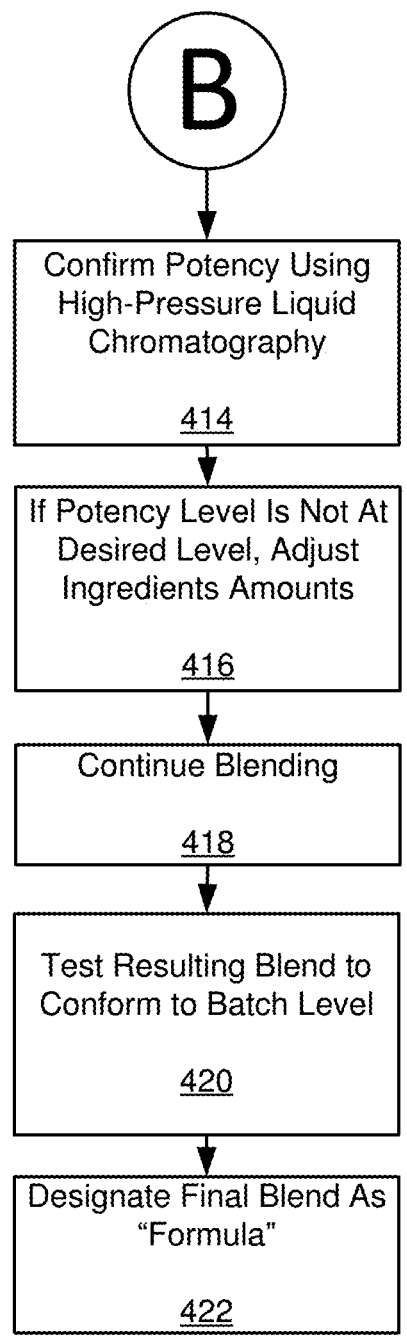
FIG. 4B is a flow chart illustrating further steps of the blending process by which the new and improved compositions are formulated.

Referring now to FIG. 4B, the method 400 continues with testing the potency levels of the resulting blend of the formulation. The potency levels of the formulation are confirmed by using a high-pressure liquid chromatography as illustrated by block 414. Once properly suspended, a sample is taken for additional testing to confirm potency utilizing high performance liquid chromatography ("HPLC"). High performance liquid chromatography is an incredibly useful analytical technique with a broad range of applications. High performance liquid chromatography is one of the most useful analytical methods in the development and manufacture of pharmaceuticals. It is instrumental in a number of critical steps necessary for robust pharmaceutical analysis, including but not limited to, evaluating formulations, checking purity, and monitoring changes due to process adjustments or during scaleup. The high-performance liquid chromatography technique is versatile and helps the (bio-) pharmaceutical researchers and manufacturing facilities fully characterize potential drug or treatment candidates, and ensure the medicines are manufactured in a safe and consistent way. Typical research experiments include understanding the chemical properties of small molecules or potential biotherapeutics, ranging from assessing the hydrophobicity of a particular molecule to the sugar structures on a monoclonal antibody that affect immune response. One specific use case is ensuring the consistency of active pharmaceutical ingredients ("API"). High performance liquid chromatography can provide quantitative analysis of select molecules, so you can confirm the correct dosage of active ingredients. For QA/QC testing, high performance liquid chromatography can be useful in ensuring critical quality attributes such as strength/concentration, content uniformity, the detection and quantification of impurities, and the quality and identity of raw materials.

If the potency level is not at the level required or desired, the ingredient levels are adjusted, as illustrated by block 416. The method 400 continues blending as illustrated by block 418. The resulting blend is tested until it reaches a level that conforms to a required or desired level for the batch, as illustrated by block 420. If the potency level for this particular composition is different than that desired, the ingredient levels are adjusted and the process continues blending until the blend tests at the appropriate conforming levels for the batch being formulated. The resulting formulation is referred to as the ("Formula").

After a desired blend is achieved, it is designated as the final blend and that final blend is designated as the "Formula," as described in block 422. This operation is followed by the encapsulating process.

Figure 5:
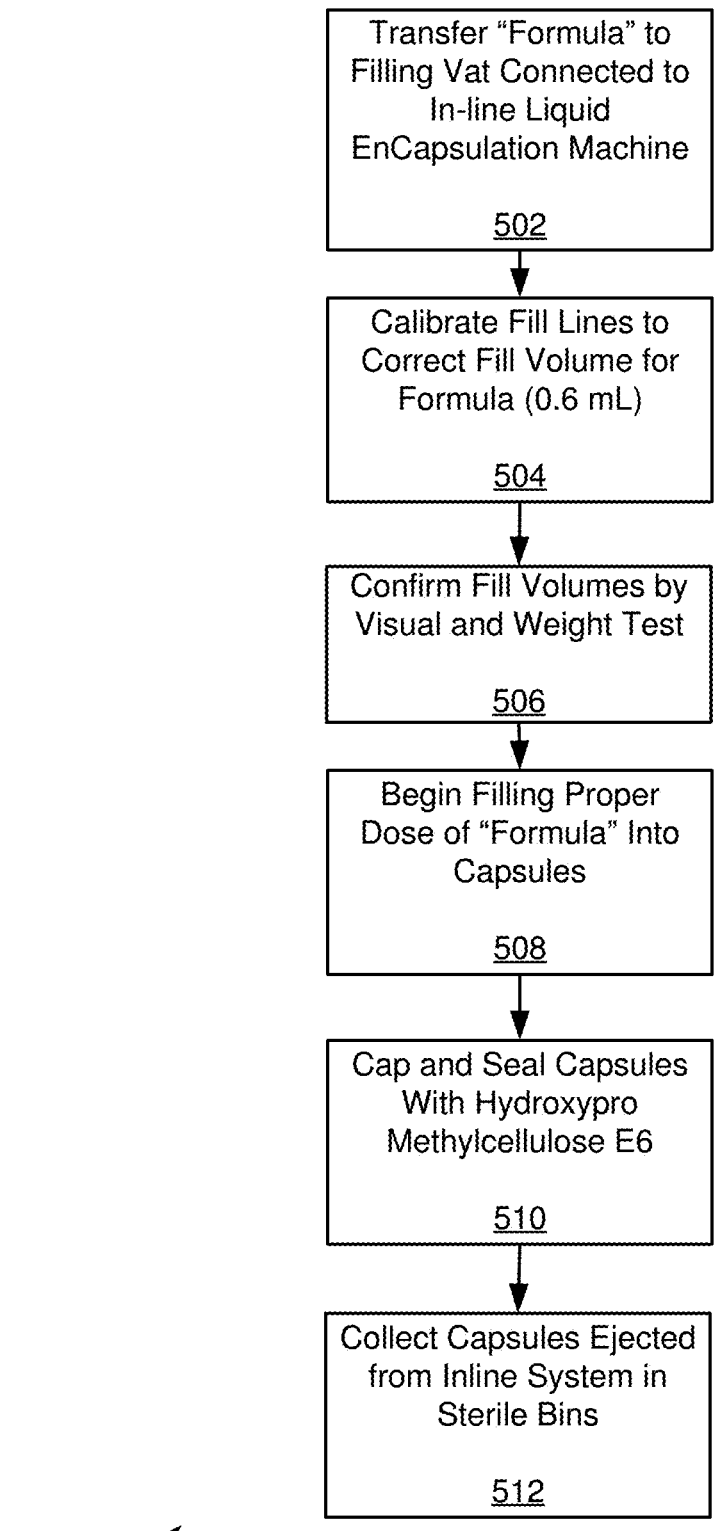
FIG. 5 is a flow chart illustrating the encapsulating process of the new formula.

Referring now to FIG. 5, a method 500 requires a transfer of the "Formula" to a filling vat connected to an inline liquid capsulation machine as illustrated and described by block 502. The Formula is subsequently transferred to the "filling" vat, which is attached to the DEA registered in-line registered liquid encapsulation machine. The method 500 calibrates fill lines to a correct and accurate "fill volume" for the "Formula." The "fill" lines are calibrated to the correct "fill" volume. In this embodiment, the "fill volume" is determined to be 0.6 ml, as described by block 504. The method 500 involves one or more operations for confirming the "fill volumes" by performing visual and weight testing as illustrated in block 506. The method 500 proceeds to the next block 508, which illustrates steps for beginning filling the proper dose into vegetarian capsules. The method 500 involves capping and sealing the capsules with hydroxypro methylcellulose E6, as illustrated by block 510. The capsules ejected from the inline system are collected in sterile bins as described by block 512.

Figure 6:
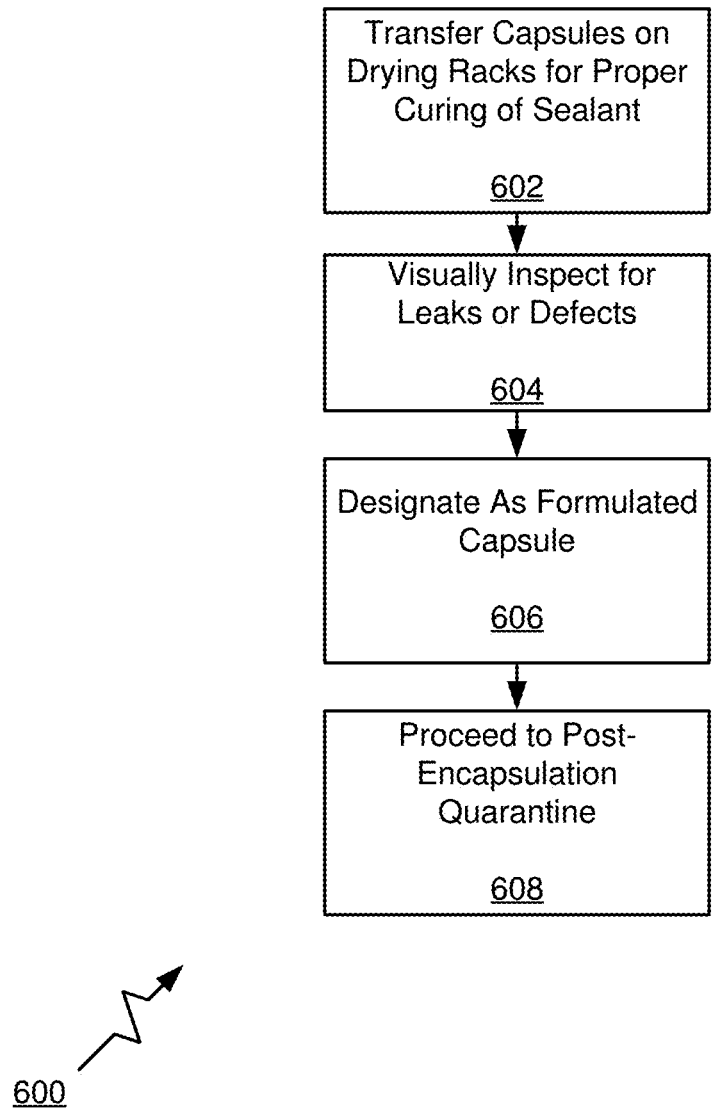
FIG. 6 is a flow chart illustrating the post-capsulation process.

Referring now the FIG. 6, the post-encapsulation process 600 starts with transferring the capsules on drying racks for proper and "full" curing of the sealant used, as illustrated by block 602. The post-encapsulation requires visually inspecting the capsules formulated with the "Formula" for visually inspecting them for leaks or defects, as described by block 604. Once the inspection confirms that the capsules have no leaks or defects, the formulated capsules are designated as "Formulated Capsules" as described by block 606. The final steps in this post-encapsulation process 600 involve proceeding to the post-encapsulation quarantine, described by block 608. The in-line system ejects the capsules into sterile bins, which are then transferred into drying racks for proper curing of the sealant and for visually inspection for leaks or defects. The resulting products are then referred to as "Formulated Capsules."

In some embodiments, the formula may be provided as formulated tablets. To formulate tablets, the "Formula" is transferred to a feeding hopper, which is attached to an in-line tableting machine. The droppers are calibrated to the correct fill volume (e.g., 400 mg) and fill volumes by a visual and weight test. When a determination is made that the system is properly calibrated, the machine drops the correct dose into the lower punch, which then is compressed into a tablet from pressure from the upper punch. For some formulations, a coating is added, which is derived from at least one of a group of: acacia, gelatin, or cellulose, which is completed in-line. The system then is configured to eject the tablets into sterile bins, which may be visually inspected for detects. By this process, formulated tablets based on the "Formula" composed are formed.

Figure 7:
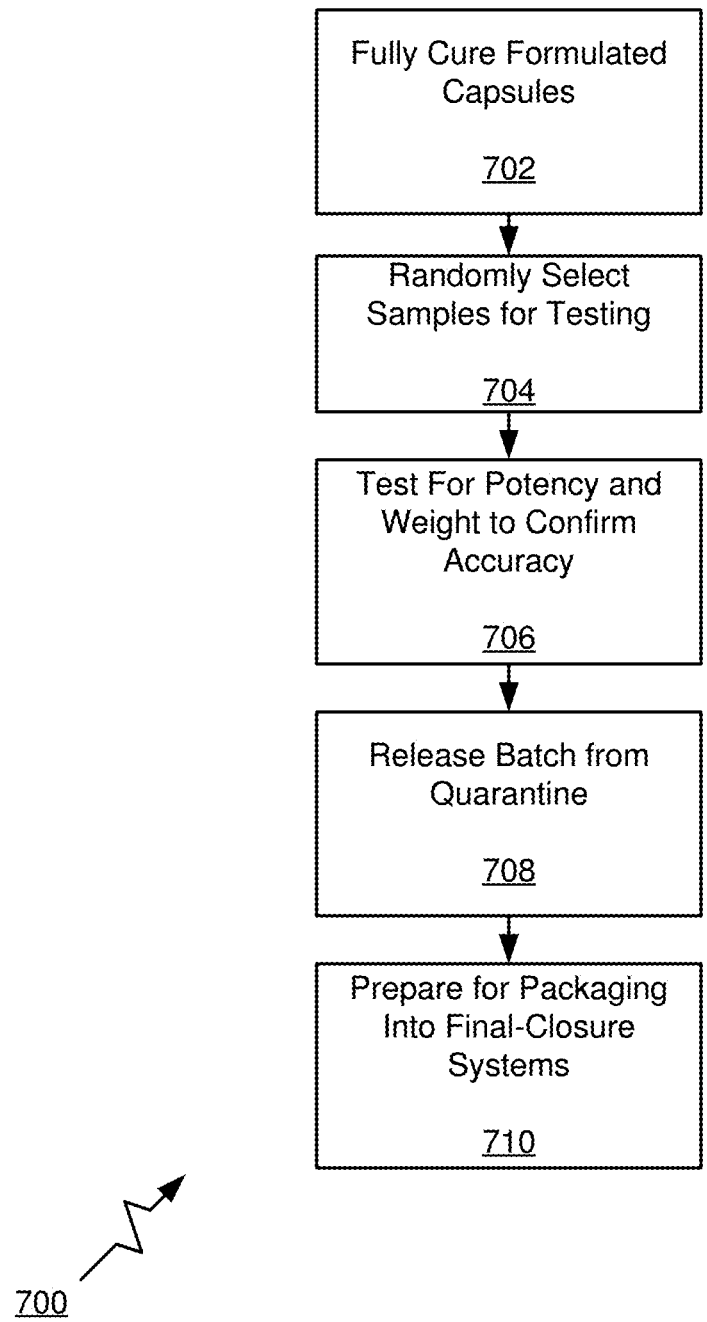
FIG. 7 is a flow chart illustrating the "quality control" process of preparing the formulated capsules with the new and improved compositions.

Referring now to FIG. 7, the next steps focus on moving to the packaging operations. The method 700 requires operations for taking the fully cured formulated capsules, as illustrated by block 702 and randomly selecting samples for testing as illustrated by block 704. The samples are tested for potency and weight to confirm accuracy as described by block 706. Once the potency levels and weight amounts are confirmed, each batch is released from quarantine, as illustrated by block 708. The final steps and operations involve preparing the batches for packaging into final closure systems, as illustrated by block 710.

Figure 8:
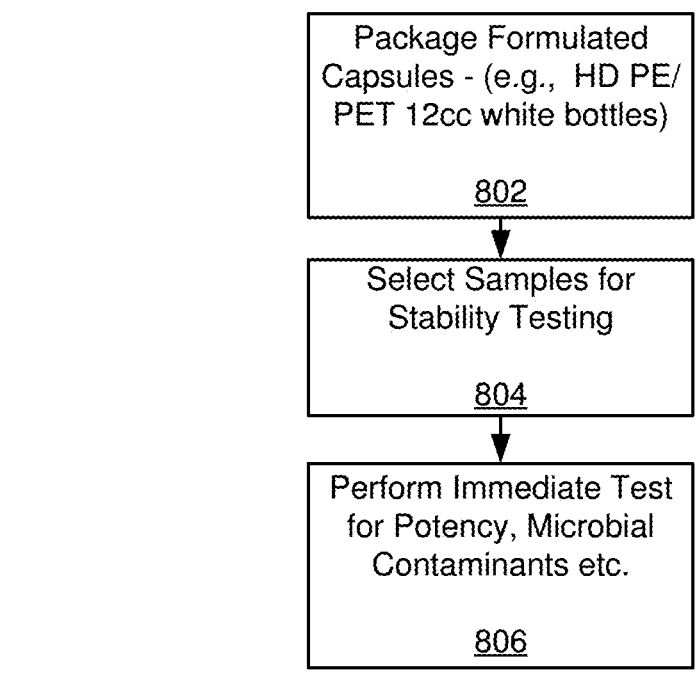
FIG. 8 is a flow chart illustrating the testing and packaging process for the new and improved compositions.
Figure 8:

Referring now to FIG. 8, the method 800 for packaging is described. For some embodiments, the formulated capsules are packaged into twelve cubic centimeter ("cc"), white HD PE/PET bottles, as illustrated by 802. Other sized bottles or suitable ways of packaging may be used instead. The packaging may be selected to meet desired criteria. In another example, formulated tablets may be packaged into 60 cc-160 cc White HDPE/PET bottles Following this, samples are again selected for stability testing as illustrated by block 804. Immediate tests for potency and microbial contaminants are performed as illustrated by block 806.

Figure 9:
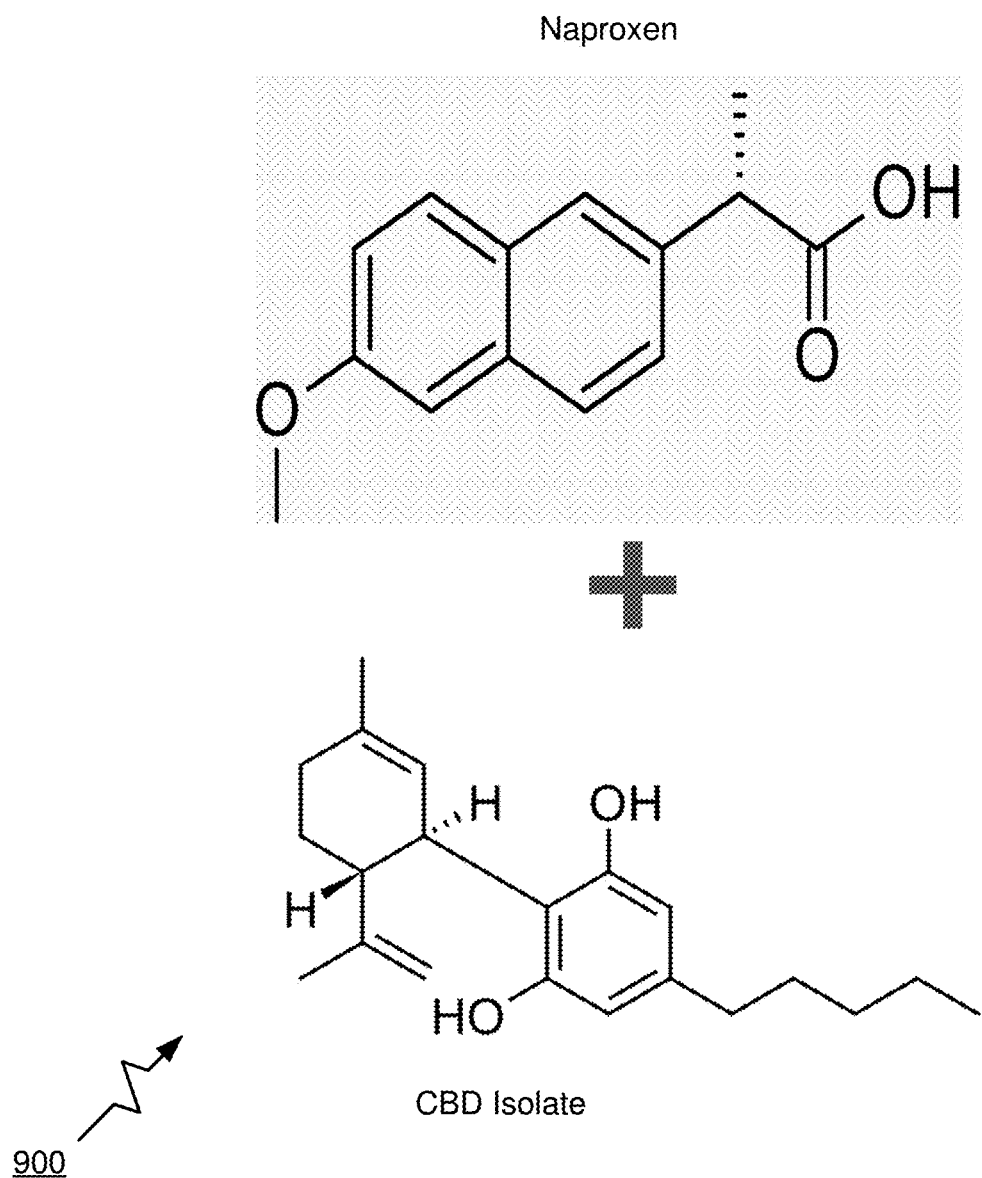
FIG. 9 illustrates the chemical structures of naproxen and the CBD isolate used to formulate the new and improved blended composition in accordance with the present invention.

FIG. 9 illustrates the chemical structures for naproxen and CBD isolate, which is one example of an improved combined formulation created in accordance with the present invention. As illustrated in FIG. 2A, the naproxen and CBD isolate blend is named here as "NP Composition r" (which may be formulated in potency levels with 0.25 of 100 mg-1500 mg of active ingredients only). The naproxen sodium and CBD isolate blend is named "NP Composition II" (which may be formulated in potency levels with 0.25 of 220 mg-1500 mg of active ingredients only). The process of formulating these particular compositions or formulations involves mixing the ingredients by blending them at a temperature between 60-80 degrees Celsius. The method of formulation breaks down the hemp active ingredient with the carrier oil to create a stable and suspended drug substance. The composition or formulation serves as an anti-inflammatory. It also advantageously serves to decrease vulnerability to addiction to opioids and it reduces the side effects compared to current Opelousas pain treatment. These improved compositions or formulations are non-intoxicating and not addictive.

Figure 10:
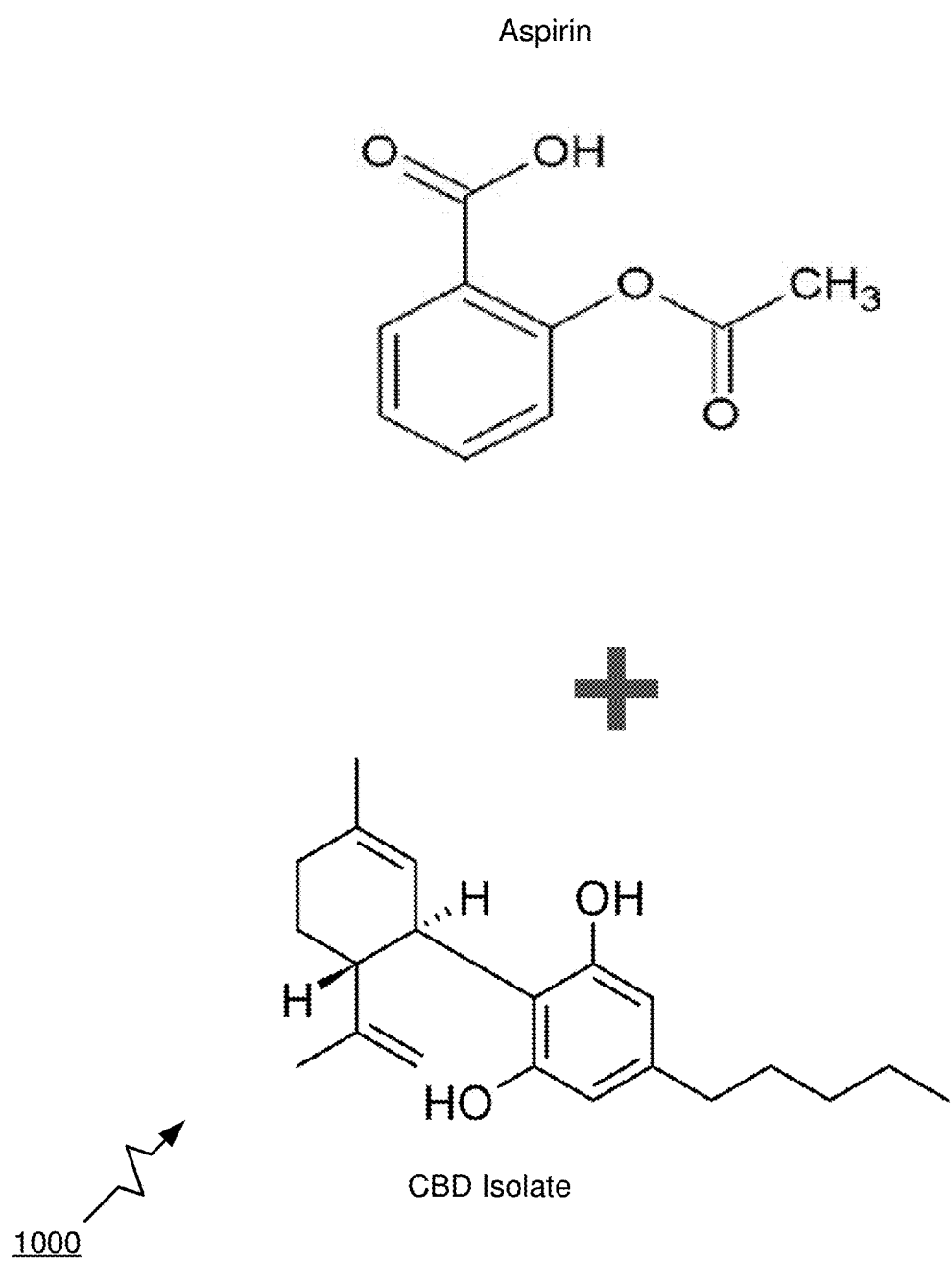
FIG. 10 illustrates the chemical structures of aspirin and the CBD isolate used to formulate the new and improved blended composition in accordance with the present invention.

FIG. 10 at 1000 illustrates the chemical structures for aspirin and CBD isolate. This is another example of an improved blend formulation created in accordance with the present invention. As illustrated in FIG. 2B, the aspirin and CBD isolate blend is named here as "AS Composition" (which may be formulated in potency levels with 0.25 of 50 mg-6000 mg of active ingredients only). The process of formulating this particular composition or formulation involves mixing the ingredients by blending them at a temperature between 60-80 degrees Celsius. The method of formulation breaks down the hemp active ingredient with the carrier oil to create a stable and suspended drug substance. The composition or formulation serves as an anti-inflammatory. It also advantageously serves to decrease vulnerability to addiction to opioids and it reduces the side effects compared to current Opelousas pain treatment. These improved compositions or formulations are non-intoxicating and not addictive.

Figure 11:
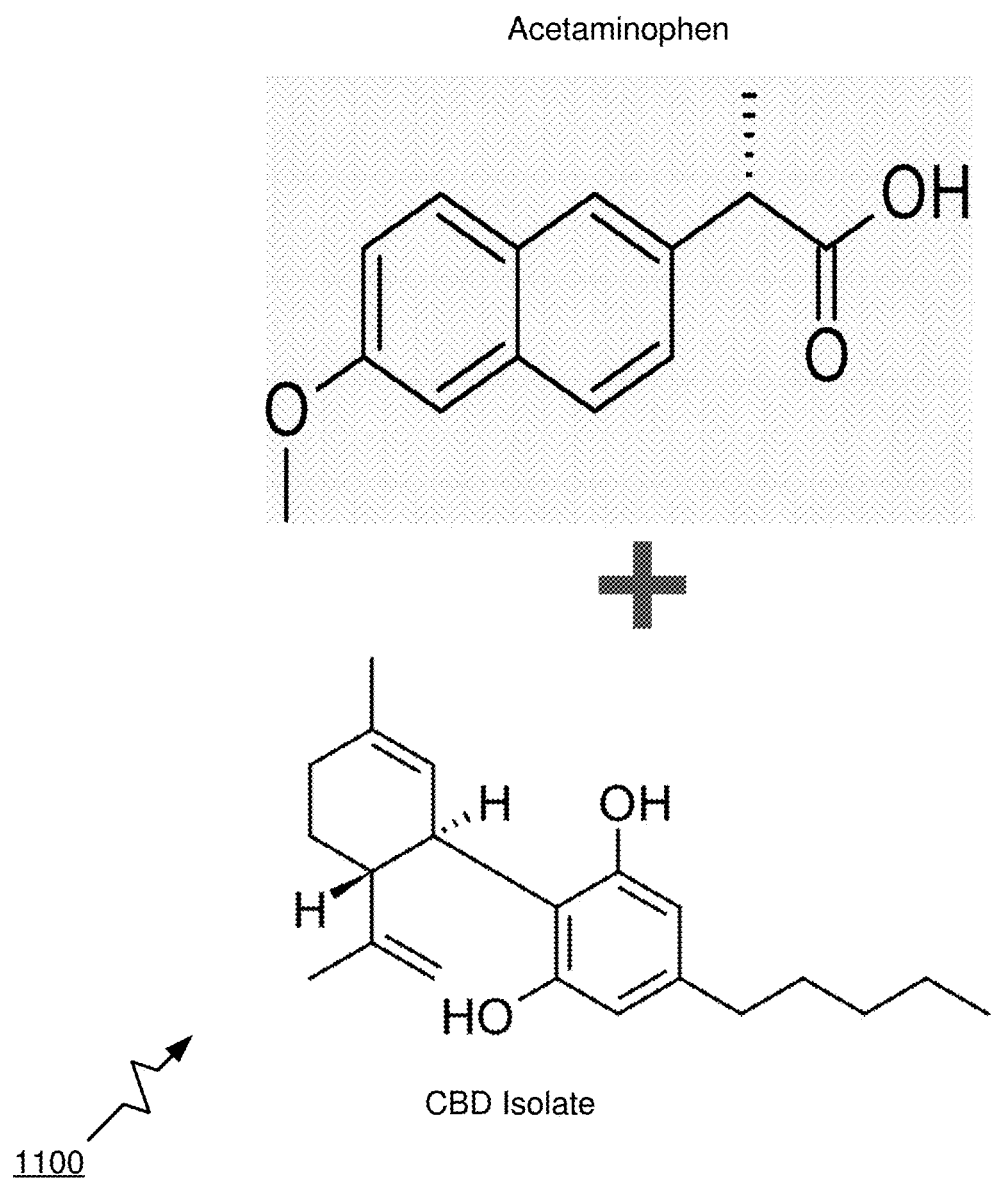
FIG. 11 illustrates the chemical structures of acetaminophen and the CBD isolate used to formulate the new and improved composition in accordance with the present invention.

FIG. 11 at 1100 illustrates the chemical structures for acetaminophen and CBD isolate. This is another example of an improved blend formulation created in accordance with the present invention. As illustrated in FIG. 2B, the acetaminophen and CBD isolate blend is named here as "AC" (which may be formulated in potency levels with 0.25 of 325 mg-3000 mg of active ingredients only). The process of formulating this particular composition or formulation involves mixing the ingredients by blending them at a temperature between 60-80 degrees Celsius. The method of formulation breaks down the hemp active ingredient with the carrier oil to create a stable and suspended drug substance. The composition or formulation serves as an anti-inflammatory. It also advantageously serves to decrease vulnerability to addiction to opioids and it reduces the side effects compared to current Opelousas pain treatment. These improved compositions or formulations are non-intoxicating and not addictive.

Figure 12:
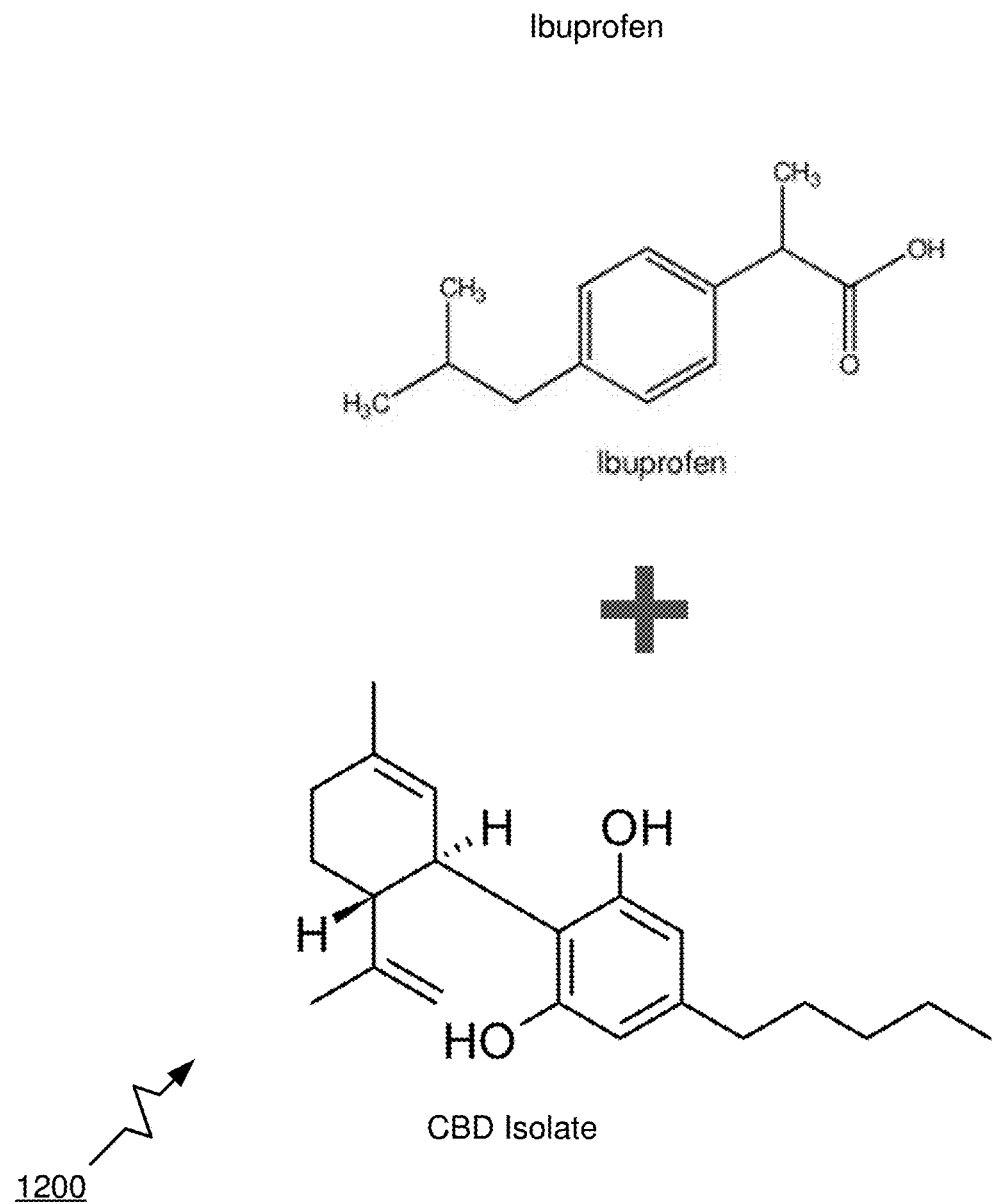
FIG. 12 illustrates the chemical structures of ibuprofen and the CBD isolate used to formulate the new composition in accordance with the present invention.

FIG. 12 at 1200 illustrates the chemical structures for ibuprofen and CBD isolate. This is another example of an improved blend formulation created in accordance with the present invention. As illustrated in FIG. 2B, the ibuprofen and CBD isolate blend is named here as "IB Composition" (which may be formulated in potency levels with 0.25 of 50 mg-3200 mg of active ingredients only). The process of formulating these particular compositions or formulations involves mixing the ingredients by blending them at a temperature between 60-80 degrees Celsius. The method of formulation breaks down the hemp active ingredient with the carrier oil to create a stable and suspended drug substance. The composition or formulation serves as an anti-inflammatory. It also advantageously serves to decrease vulnerability to addiction to opioids and it reduces the side effects compared to current Opelousas pain treatment. These improved compositions or formulations are non-intoxicating and not addictive.

Figure 13:
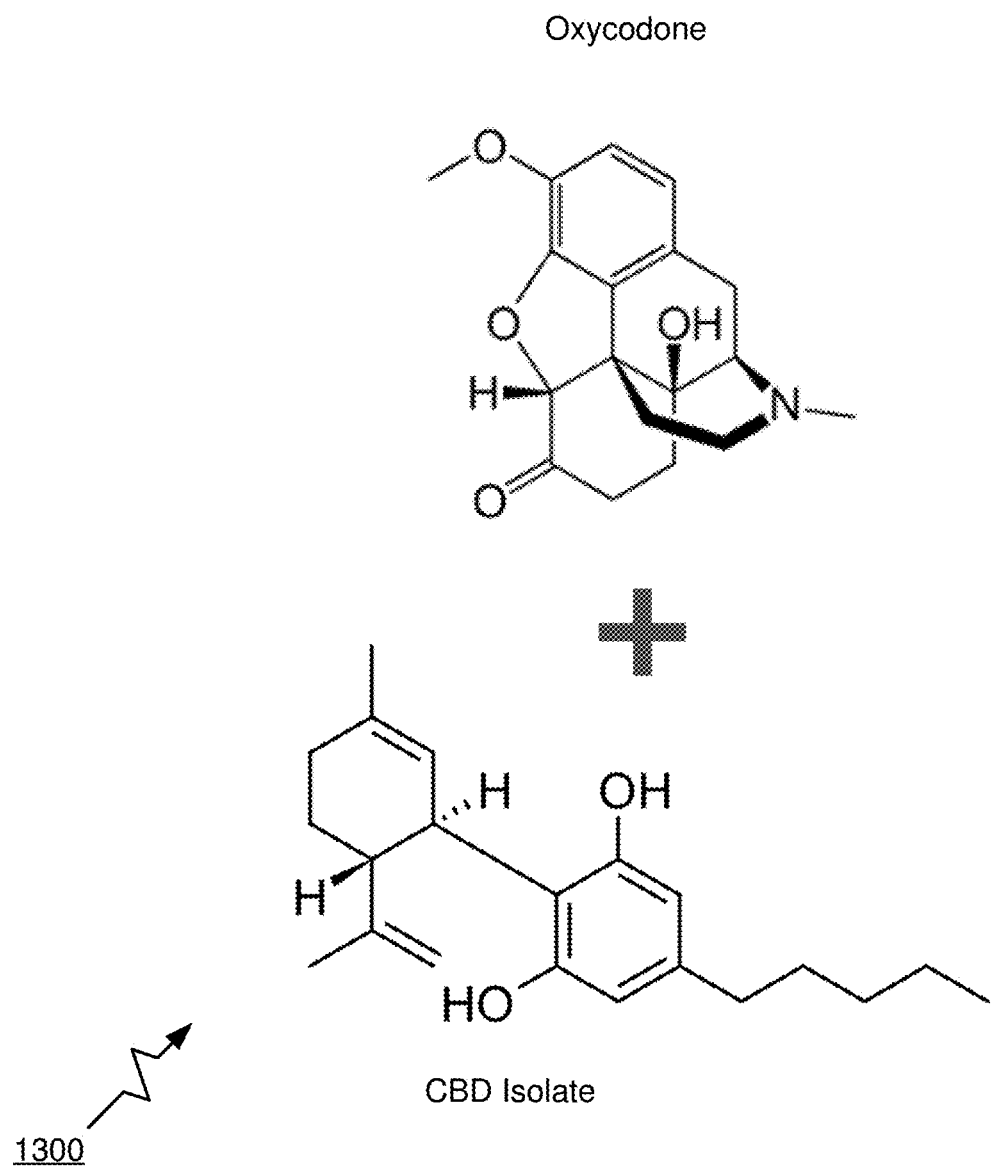
FIG. 13 illustrates the chemical structures of oxycodone and the CBD isolate used to formulate the new composition in accordance with the present invention.

FIG. 13 at 1300 illustrates the chemical structures for oxycodone and CBD isolate. This is another example of an improved blend formulation created in accordance with the present invention to reduce the ill effects of this opioid. The blend formulation has only 0.25 of the active ingredient in oxycodone and is blended with the processes described in FIGS. 1, 3, 4A, 4B, 5, 6, 7, and 8. It is named here as "Oxycodone/CBD Isolate Blend Composition."

Figure 14:
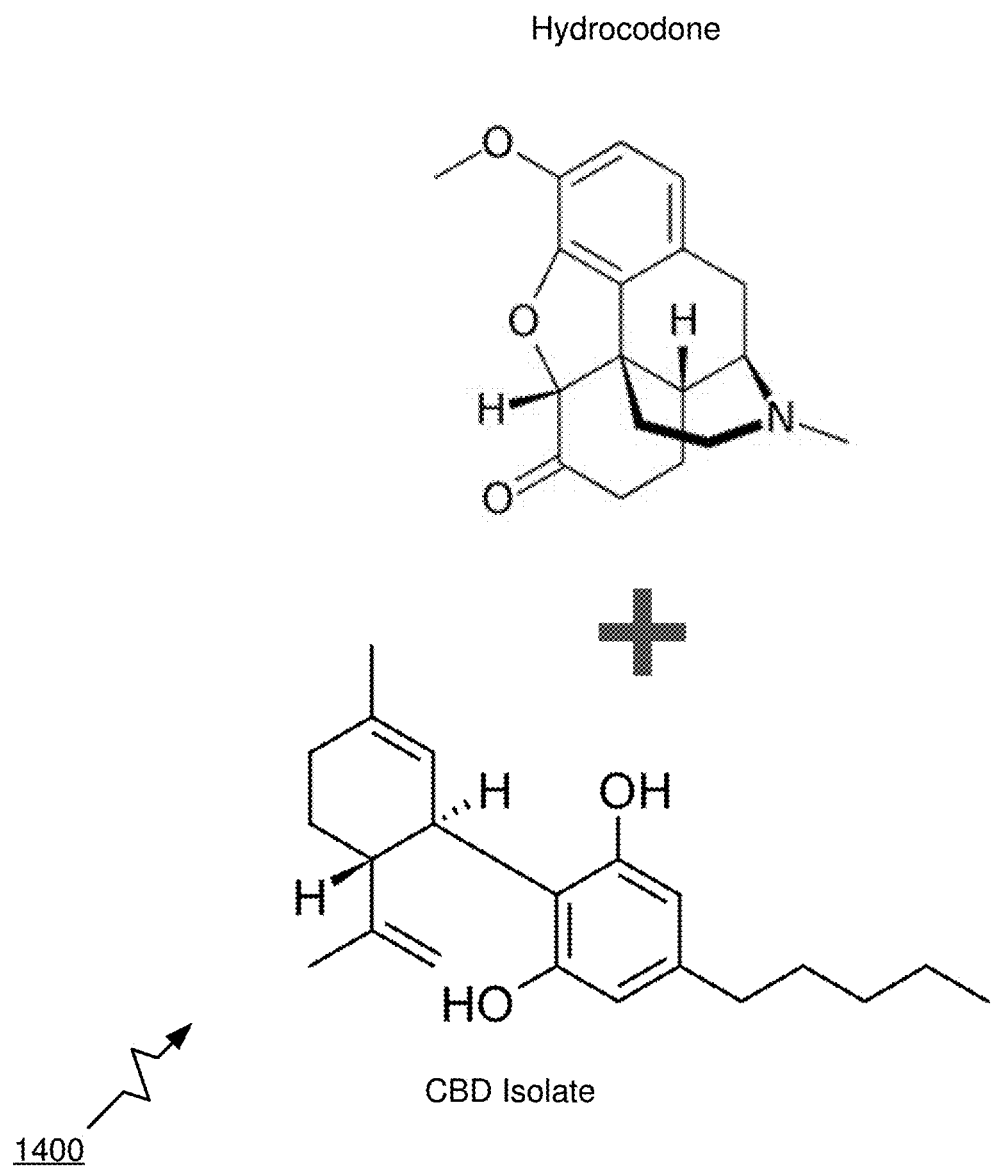
FIG. 14 illustrates the chemical structures of hydrocodone and the CBD isolate used to formulate the new composition in accordance with the present invention.

FIG. 14 at 1400 illustrates the chemical structures for hydrocodone and CBD isolate. This is another example of an improved blend formulation created in accordance with the present invention to reduce the ill effects of this opioid. The blend formulation has only 0.25 of the active ingredient in hydrocodone and is blended with the processes described in FIGS. 1, 3, 4A, 4B, 5, 6, 7, and 8. It is named here as "Hydrocodone/CBD Isolate Blend Composition."

Figure 15:
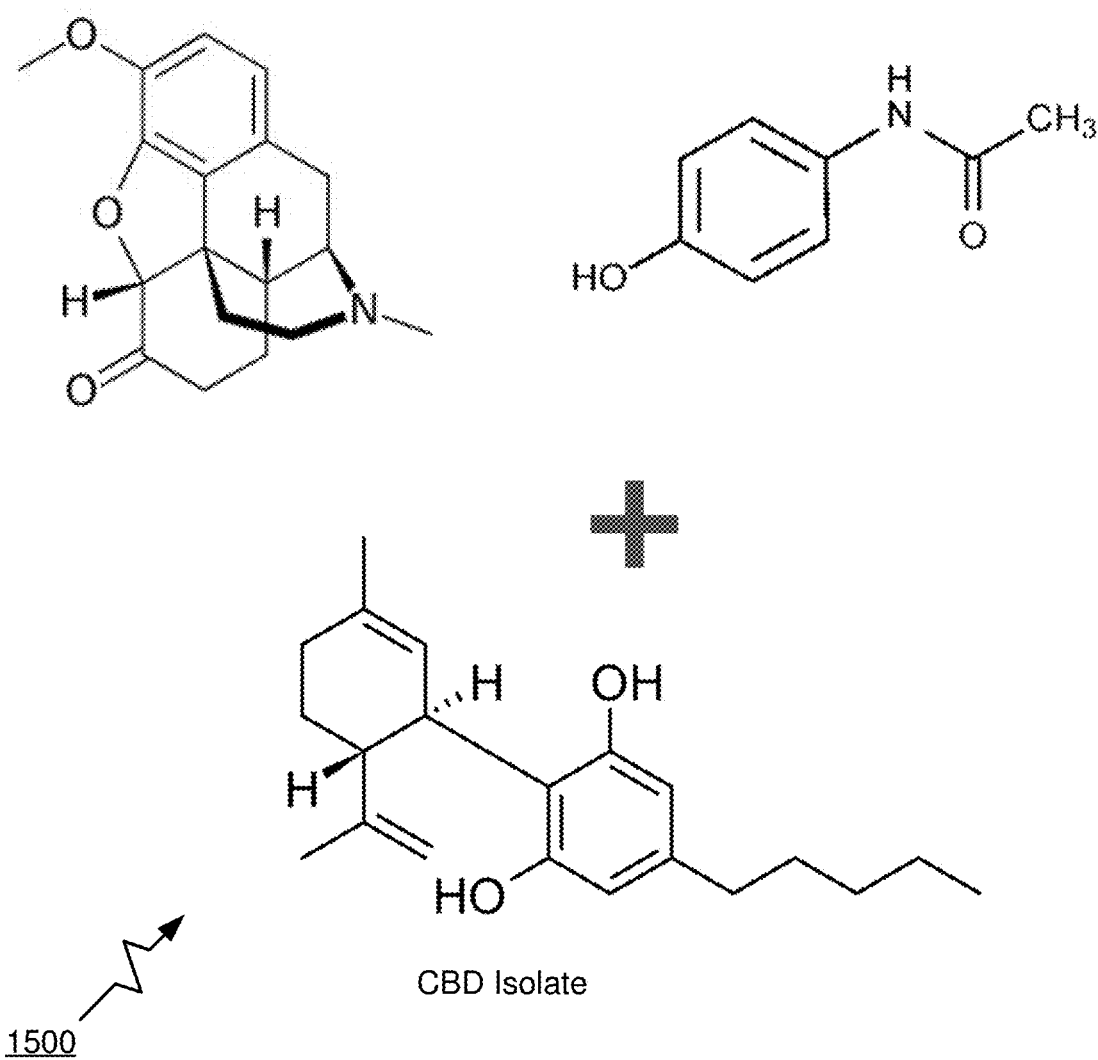
FIG. 15 illustrates the chemical structures of hydrocodone, acetaminophen, and the CBD isolate used to formulate the new composition in accordance with the present invention.

FIG. 15 at 1500 illustrates the chemical structures for hydrocodone, acetaminophen and CBD isolate. This is another example of an improved blend formulation created in accordance with the present invention to reduce the ill effects of this opioid blend. The blend formulation has only 0.25 of the active ingredients in hydrocodone and acetaminophen and is blended with the processes described in FIGS. 1, 3, 4A, 4B, 5, 6, 7, and 8. It is named here as "Hydrocodone-Acetaminophen/CBD Isolate Blend Composition."

Figure 16:
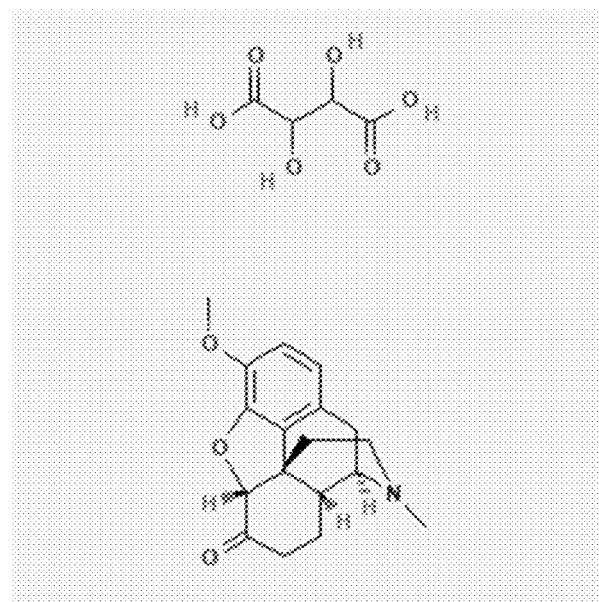
FIG. 16 illustrates the chemical structures of hydrocodone bitartrate and the CBD isolate used to formulate the new composition in accordance with the present invention.
Figure 16:
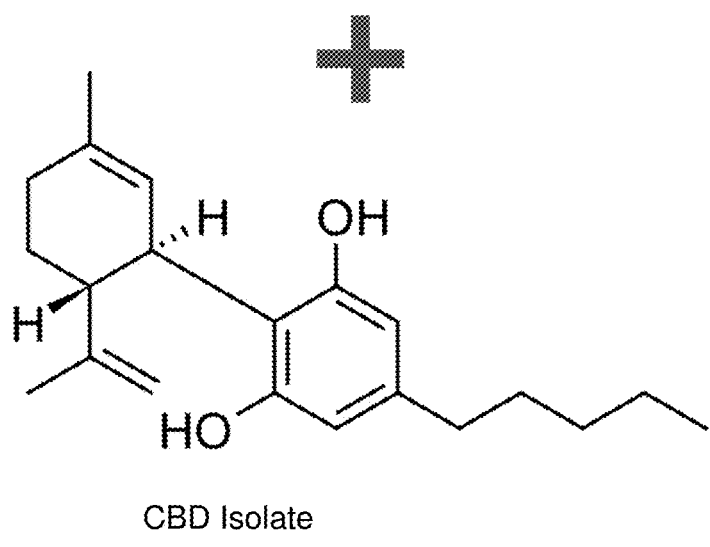

FIG. 16 at 1600 illustrates the chemical structures for hydrocodone bitartrate and CBD isolate. This is another example of an improved blend formulation created in accordance with the present invention to reduce the ill effects of this opioid blend. The blend formulation has only 0.25 of the active ingredient in hydrocodone bitartrate and is blended with the processes described in FIGS. 1, 3, 4A, 4B, 5, 6, 7, and 8. It is named here as "Hydrocodone bitartrate/CBD Isolate Blend Composition."

Figure 17:
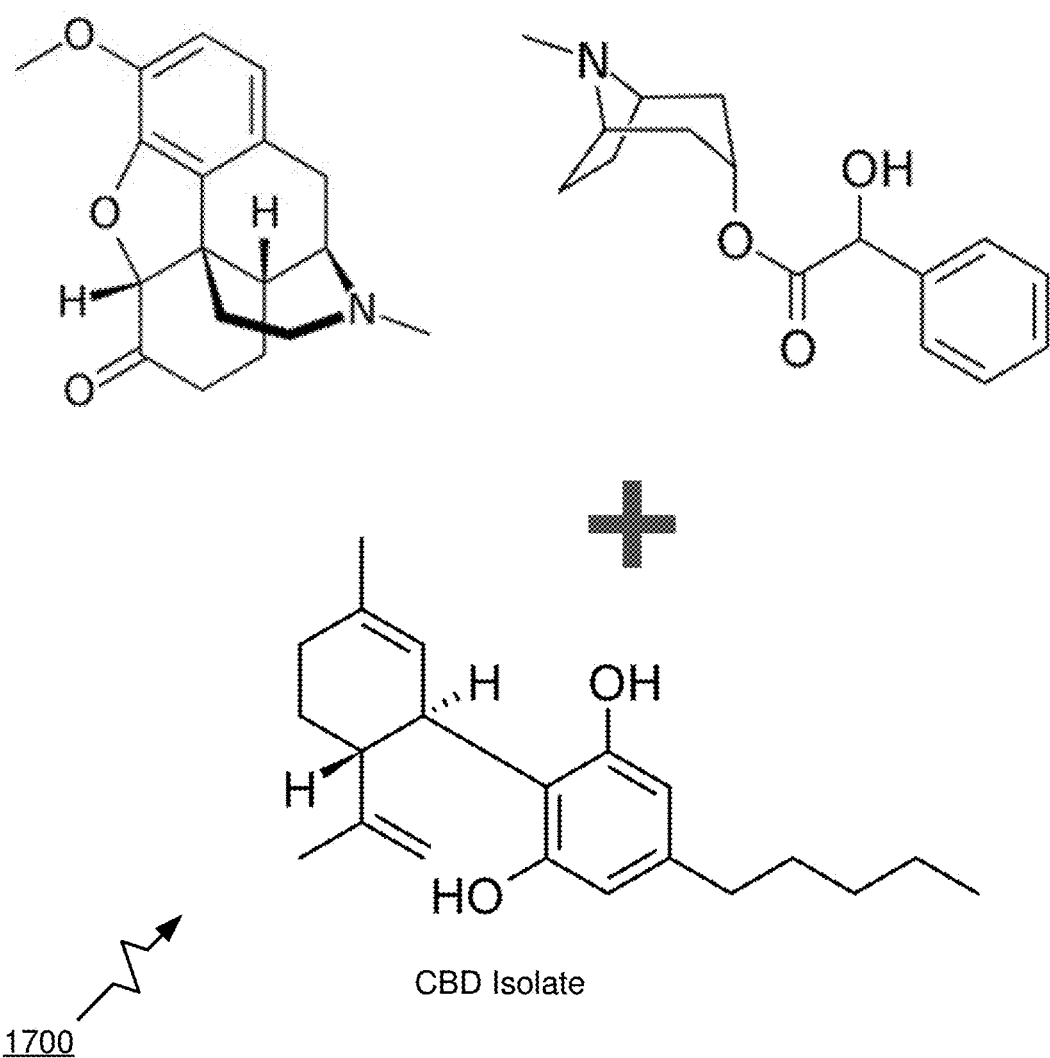
FIG. 17 illustrates the chemical structures of hydrocodone, homatropine, and the CBD isolate used to formulate the new composition in accordance with the present invention.

FIG. 17 at 1700 illustrates the chemical structures for hydrocodone, homatropine and CBD isolate. This is another example of an improved blend formulation created in accordance with the present invention to reduce the ill effects of this opioid blend. The blend formulation has only 0.25 of the active ingredients in hydrocodone and homatropine and is blended with the processes described in FIGS. 1, 3, 4A, 4B, 5, 6, 7, and 8. It is named here as "Hydrocodone-homatropine/CBD Isolate Blend Composition."

Figure 18:
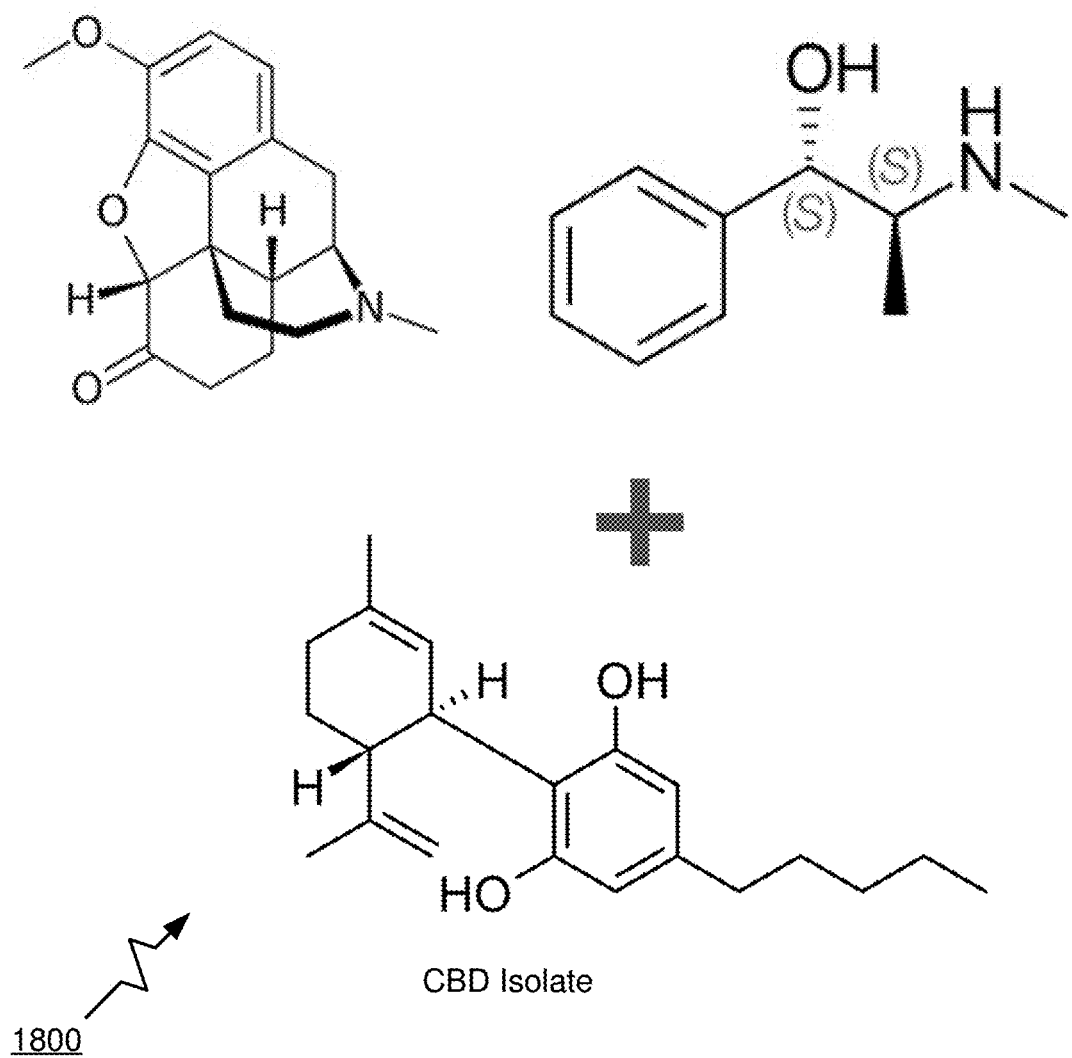
FIG. 18 illustrates the chemical structures of hydrocodone, pseudoephedrine, and the CBD isolate used to formulate the new composition in accordance with the present invention.

FIG. 18 at 1800 illustrates the chemical structures for hydrocodone, pseudoephedrine and CBD isolate. This is another example of an improved blend formulation created in accordance with the present invention to reduce the ill effects of this opioid blend. The blend formulation has only 0.25 of the active ingredients in hydrocodone and pseudoephedrine and is blended with the processes described in FIGS. 1, 3, 4A, 4B, 5, 6, 7, and 8. It is named here as "Hydrocodone-pseudoephedrine/CBD Isolate Blend Composition."

Figure 19:
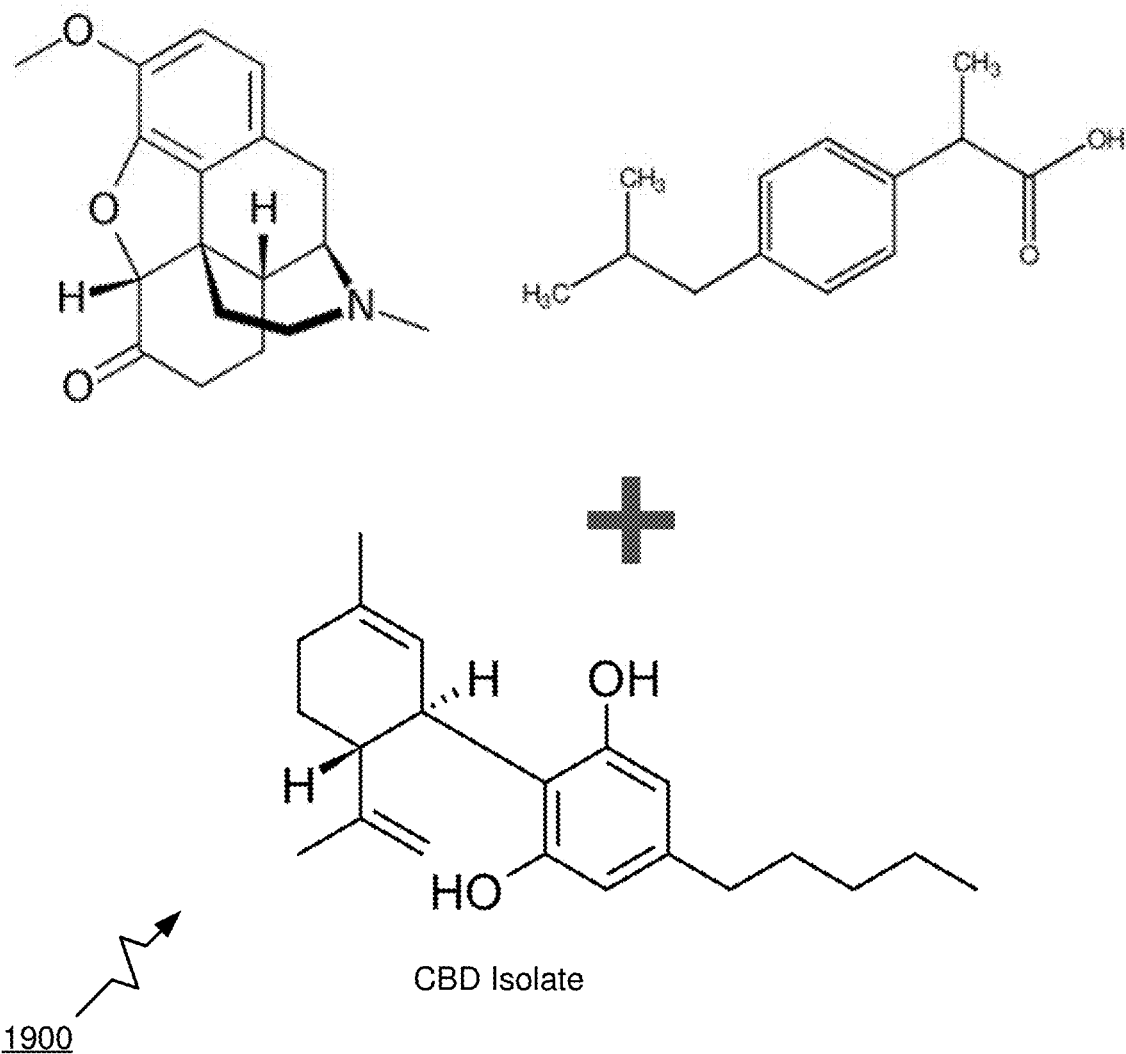
FIG. 19 illustrates the chemical structures of hydrocodone, ibuprofen and the CBD isolate used to formulate the new composition in accordance with the present invention.

FIG. 19 at 1900 illustrates the chemical structures for hydrocodone, ibuprofen and CBD isolate. This is another example of an improved blend formulation created in accordance with the present invention to reduce the ill effects of this opioid blend. The blend formulation has only 0.25 of the active ingredients in hydrocodone and ibuprofen and is blended with the processes described in FIGS. 1, 3, 4A, 4B, 5, 6, 7, and 8. It is named here as "Hydrocodone-ibuprofen/CBD Isolate Blend Composition."

Figure 20:
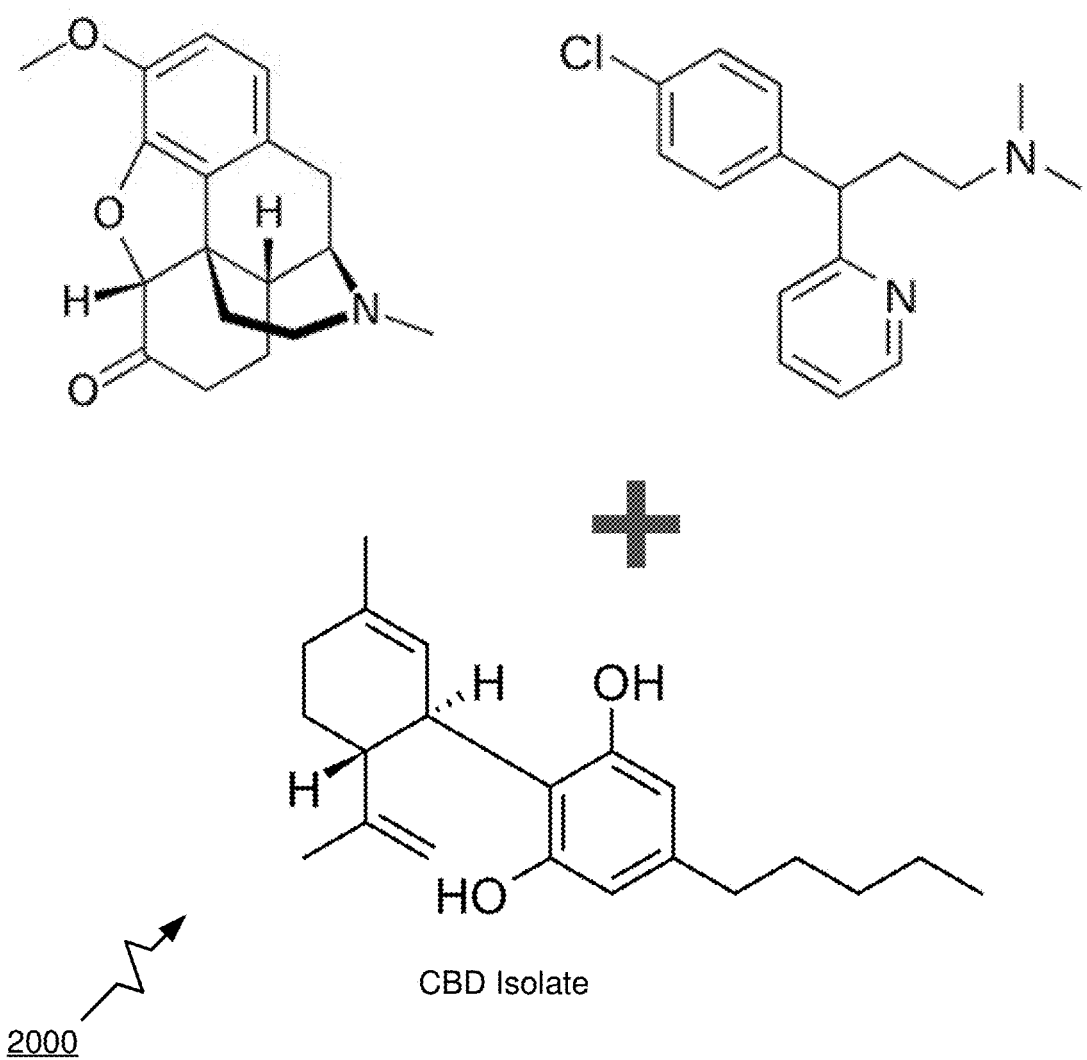
FIG. 20 illustrates the chemical structures of hydrocodone, chlorpheniramine, and the CBD isolate used to formulate the new composition in accordance with the present invention.

FIG. 20 at 2000 illustrates the chemical structures for hydrocodone, chlorpheniramine and CBD isolate. This is another example of an improved blend formulation created in accordance with the present invention to reduce the ill effects of this opioid blend. The blend formulation has only 0.25 of the active ingredients in hydrocodone and chlorpheniramine and is blended with the processes described in FIGS. 1, 3, 4A, 4B, 5, 6, 7, and 8. It is named here as "Hydrocodone-chlorpheniramine/CBD Isolate Blend Composition."

Figure 21:
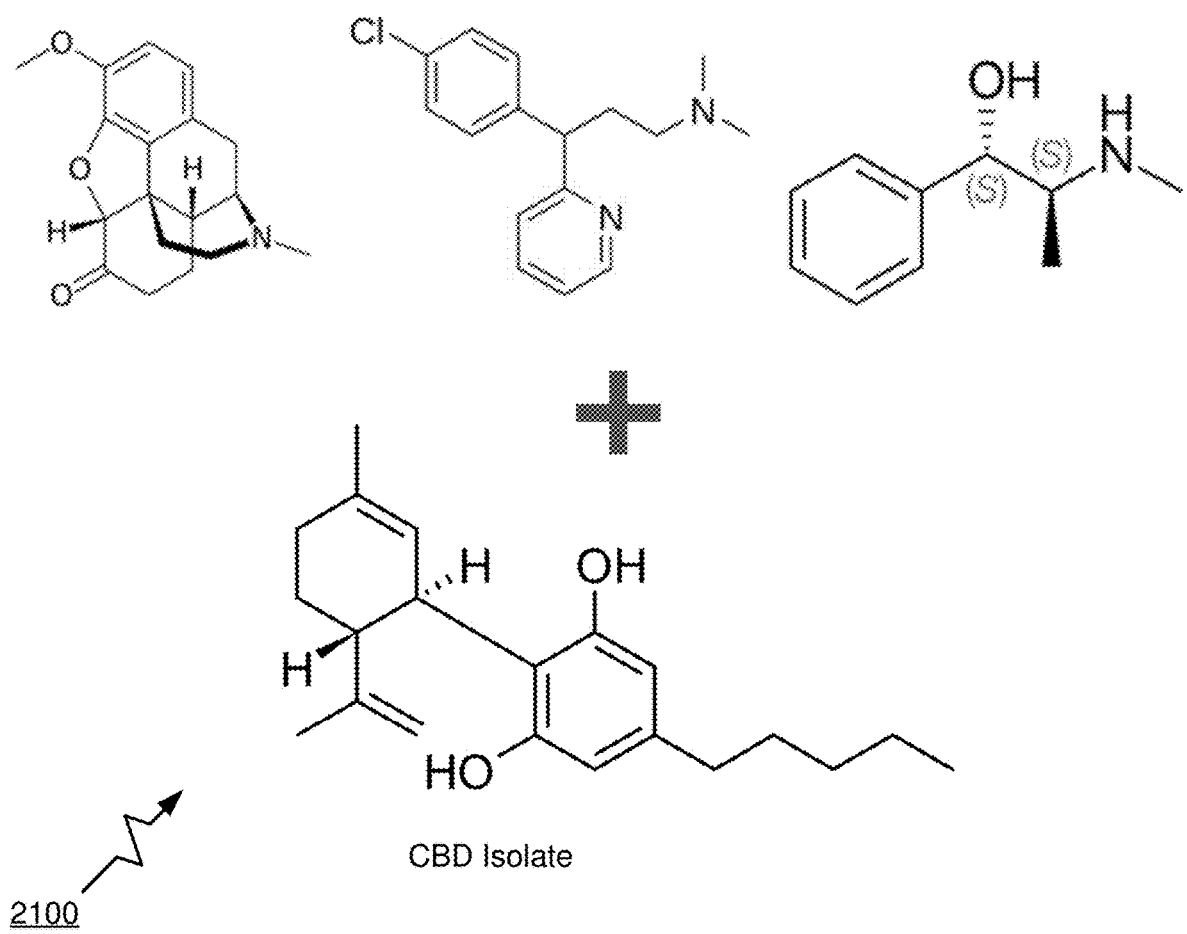
FIG. 21 illustrates the chemical structures of hydrocodone, chlorpheniramine, pseudoephedrine and the CBD isolate used to formulate the new composition in accordance with the present invention.

FIG. 21 at 2100 illustrates the chemical structures for hydrocodone, chlorpheniramine and pseudoephedrine and CBD isolate. This is another example of an improved blend formulation created in accordance with the present invention to reduce the ill effects of this opioid blend. The blend formulation has only 0.25 of the active ingredients in hydrocodone, chlorpheniramine and pseudoephedrine and is blended with the processes described in FIGS. 1, 3, 4A, 4B, 5, 6, 7, and 8. It is named here as "Hydrocodone-chlorpheniramine-pseudoephedrine/CBD Isolate Blend Composition."

Figure 22:
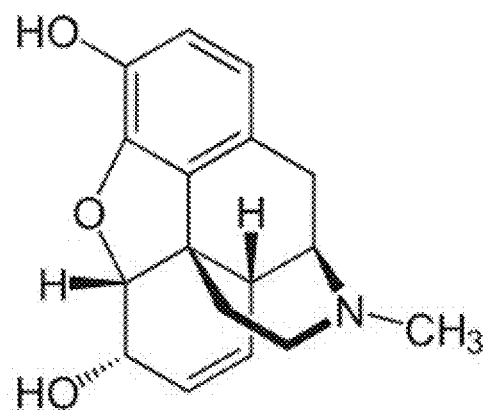
FIG. 22 illustrates the chemical structures of morphine and the CBD isolate used to formulate the new composition in accordance with the present invention.
Figure 22:
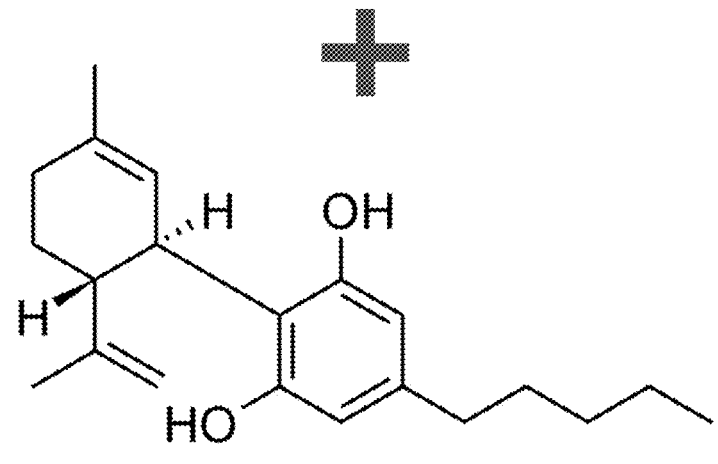

FIG. 22 at 2200 illustrates the chemical structures for morphine and CBD isolate. This is another example of an improved blend formulation created in accordance with the present invention to reduce the ill effects of this opioid blend. The blend formulation has only 0.25 of the active ingredient in morphine and is blended with the processes described in FIGS. 1, 3, 4A, 4B, 5, 6, 7, and 8. It is named here as "Morphine/CBD Isolate Blend Composition."

Figure 23:
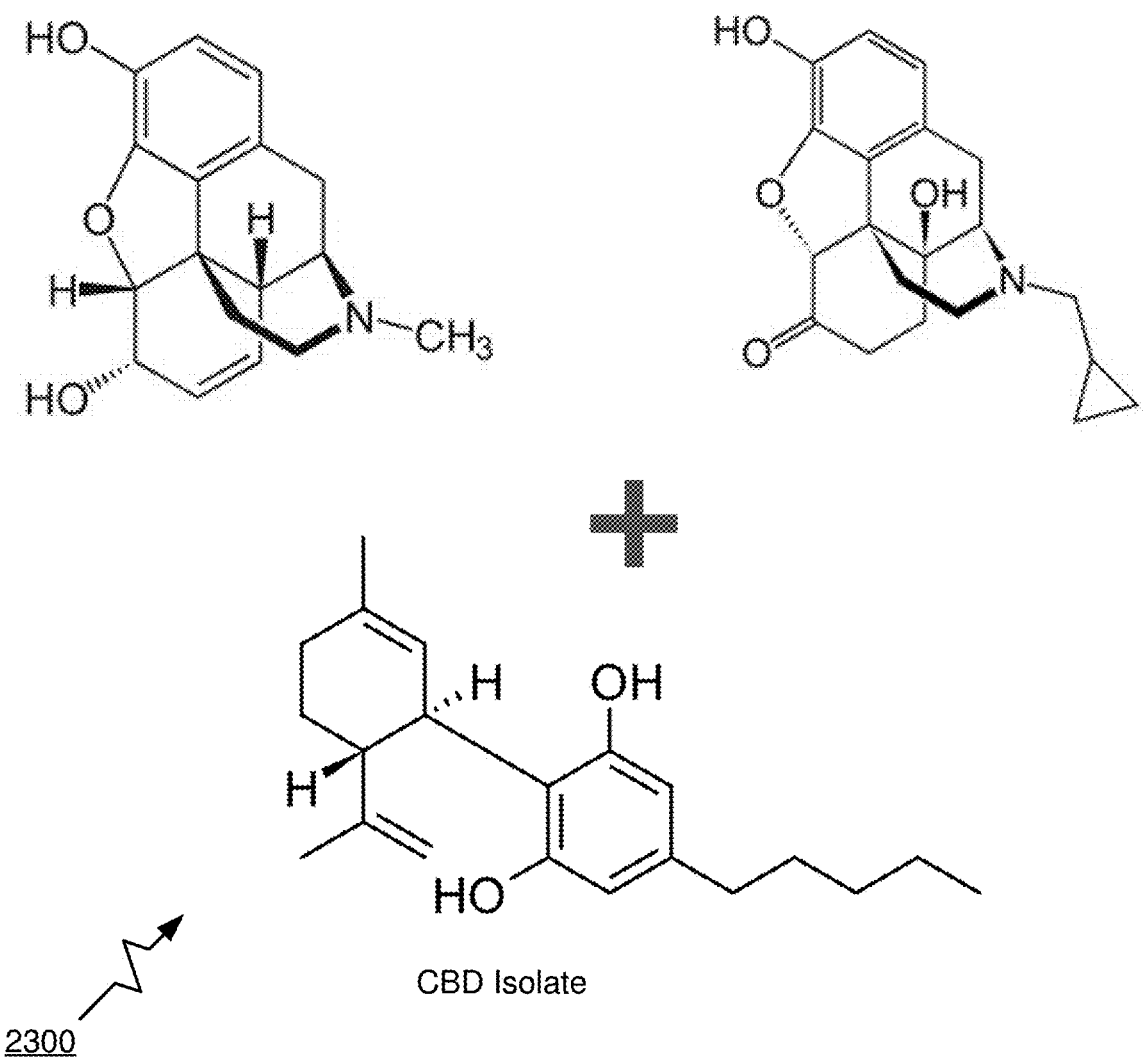
FIG. 23 illustrates the chemical structures of morphine, naltrexone and the CBD isolate used to formulate the new composition in accordance with the present invention.

FIG. 23 at 2300 illustrates the chemical structures for morphine, naltrexone and CBD isolate. This is another example of an improved blend formulation created in accordance with the present invention to reduce the ill effects of this opioid blend. The blend formulation has only 0.25 of the active ingredients in morphine and naltrexone and is blended with CBD isolate with the processes described in FIGS. 1, 3, 4A, 4B, 5, 6, 7, and 8. It is named here as "Morphine-naltrexone/CBD Isolate Blend Composition."

Figure 24:
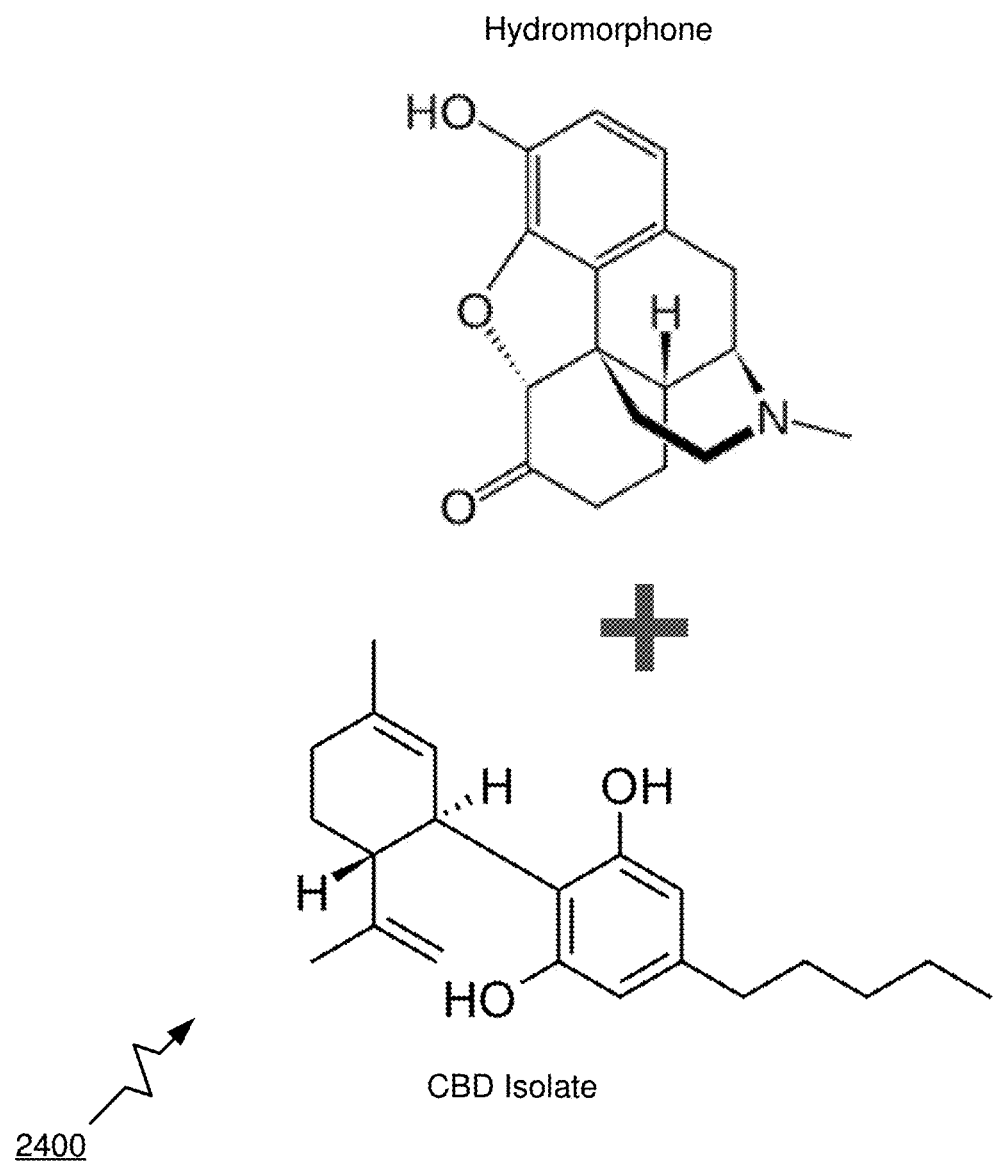
FIG. 24 illustrates the chemical structures of hydromorphone and the CBD isolate used to formulate the new composition in accordance with the present invention.

FIG. 24 at 2400 illustrates the chemical structures for Hydromorphine and CBD isolate. This is another example of an improved blend formulation created in accordance with the present invention to reduce the ill effects of this opioid blend. The blend formulation has only 0.25 of the active ingredients in hydromorphine and CBD isolate and is blended with the processes described in FIGS. 1, 3, 4A, 4B, 5, 6, 7, and 8. It is named here as "hydromorphine/CBD Isolate Blend Composition."

Figure 25:
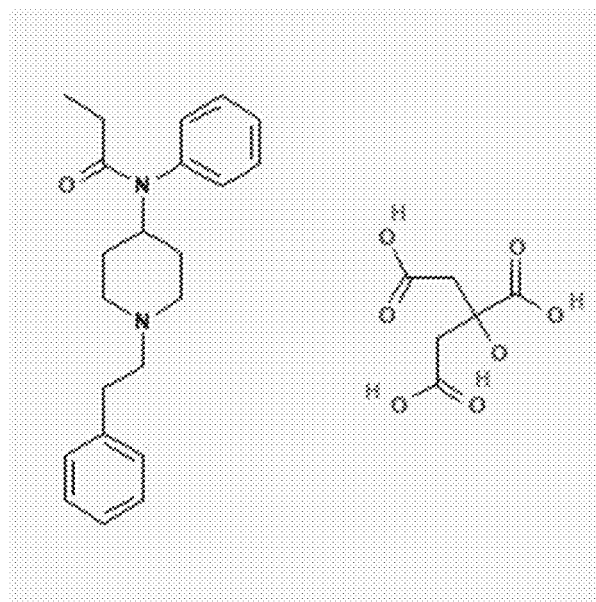
FIG. 25 illustrates the chemical structures of fentanyl citrate and the CBD isolate used to formulate the new composition in accordance with the present invention.
Figure 25:
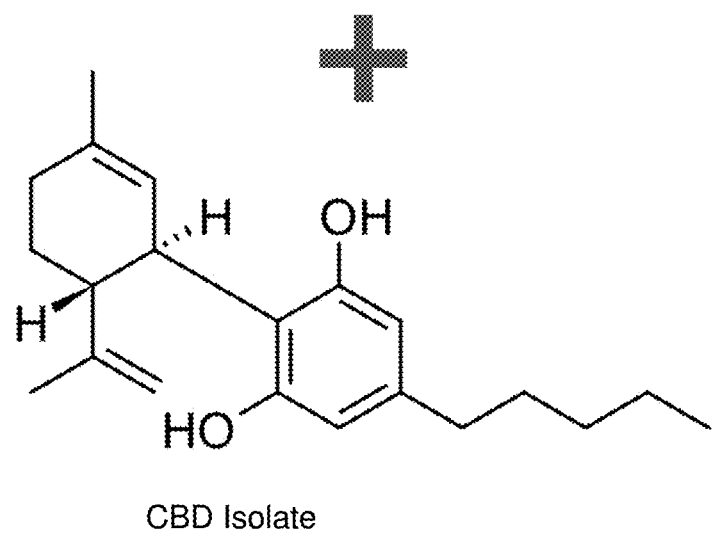

FIG. 25 at 2500 illustrates the chemical structures for fentanyl citrate and CBD isolate. This is another example of an improved blend formulation created in accordance with the present invention to reduce the ill effects of this opioid blend. The blend formulation has only 0.25 of the active ingredients in fentanyl citrate and CBD isolate and is blended with the processes described in FIGS. 1, 3, 4A, 4B, 5, 6, 7, and 8. It is named here as "fentanyl-citrate/CBD Isolate Blend Composition."

Figure 26:
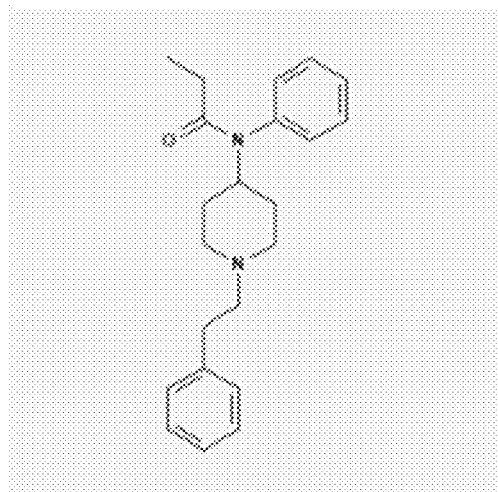
FIG. 26 illustrates the chemical structures of fentanyl and the CBD isolate used to formulate the new composition in accordance with the present invention.
Figure 26:
Figure 26:
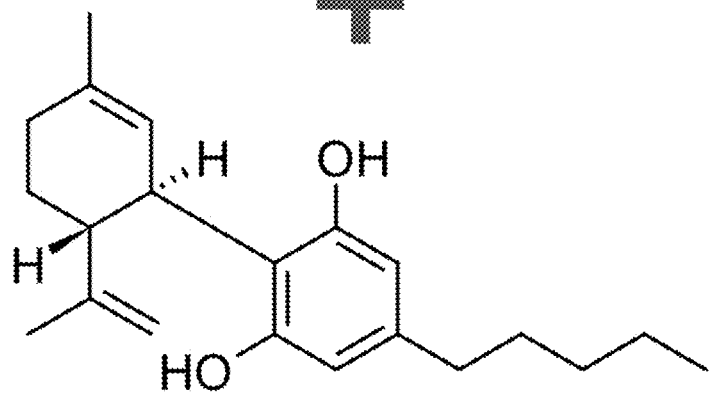

FIG. 26 at 2600 illustrates the chemical structures for fentanyl and CBD isolate. This is another example of an improved blend formulation created in accordance with the present invention to reduce the ill effects of this opioid blend. The blend formulation has only 0.25 of the active ingredients in fentanyl and CBD isolate and is blended with the processes described in FIGS. 1, 3, 4A, 4B, 5, 6, 7, and 8. It is named here as "Fentanyl/CBD Isolate Blend Composition."

Figure 27:
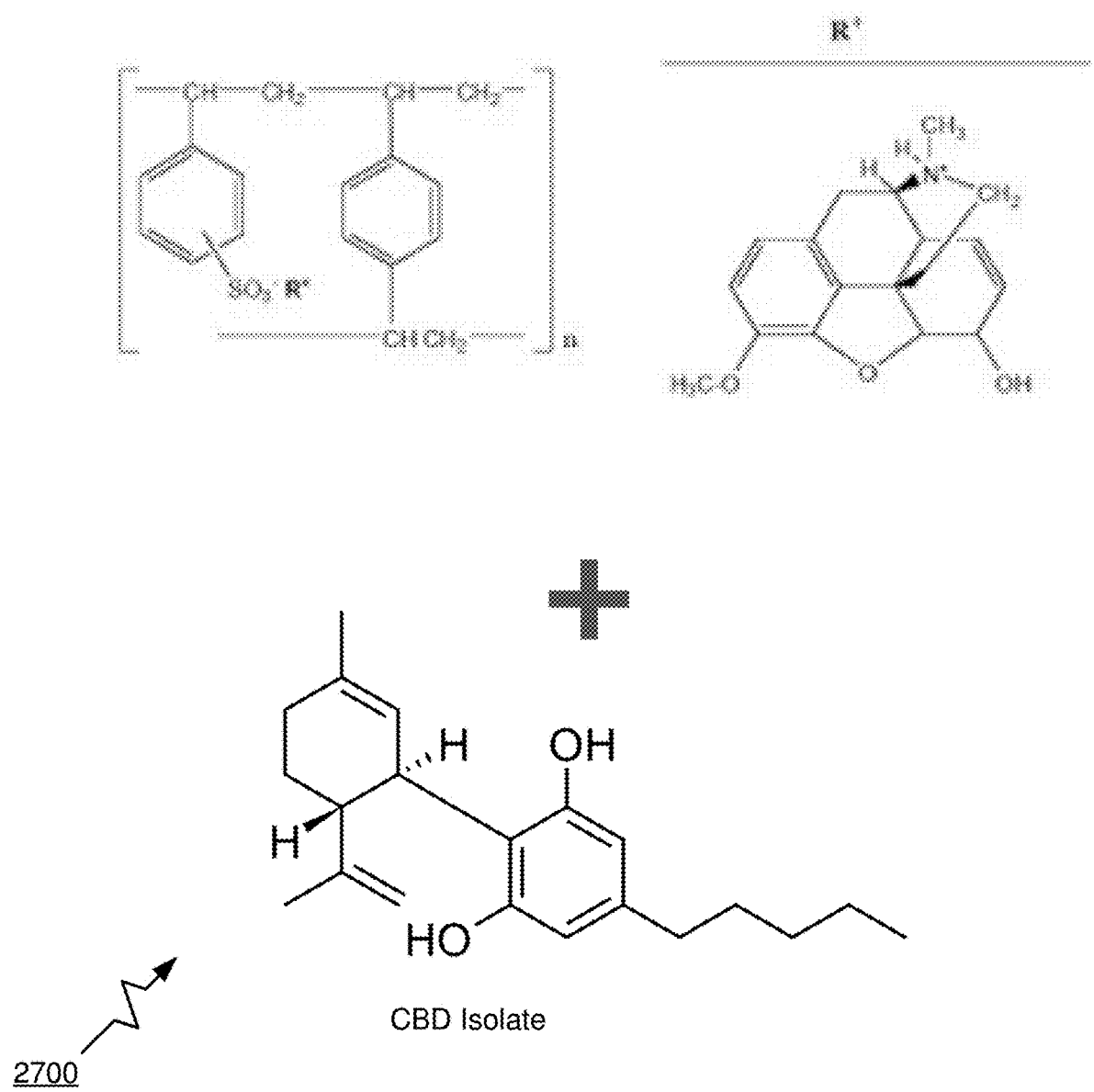
FIG. 27 illustrates the chemical structures of codeine polistirex and chlorpheniramine polistirex and the CBD isolate used to formulate the new composition in accordance with the present invention.

FIG. 27 at 2700 illustrates the chemical structures for Codeine Polistirex and Chlorpheniramine Polistirex and CBD isolate. This is another example of an improved blend formulation created in accordance with the present invention to reduce the ill effects of this opioid blend. The blend formulation has only 0.25 of the active ingredients in Codeine Polistirex and Chlorpheniramine Polistirex and CBD isolate and is blended with the processes described in FIGS. 1, 3, 4A, 4B, 5, 6, 7, and 8. It is named here as "Codeine-Polistirex-Chlorpheniramine-Polistirex/CBD Isolate Blend Composition."

Figure 28:
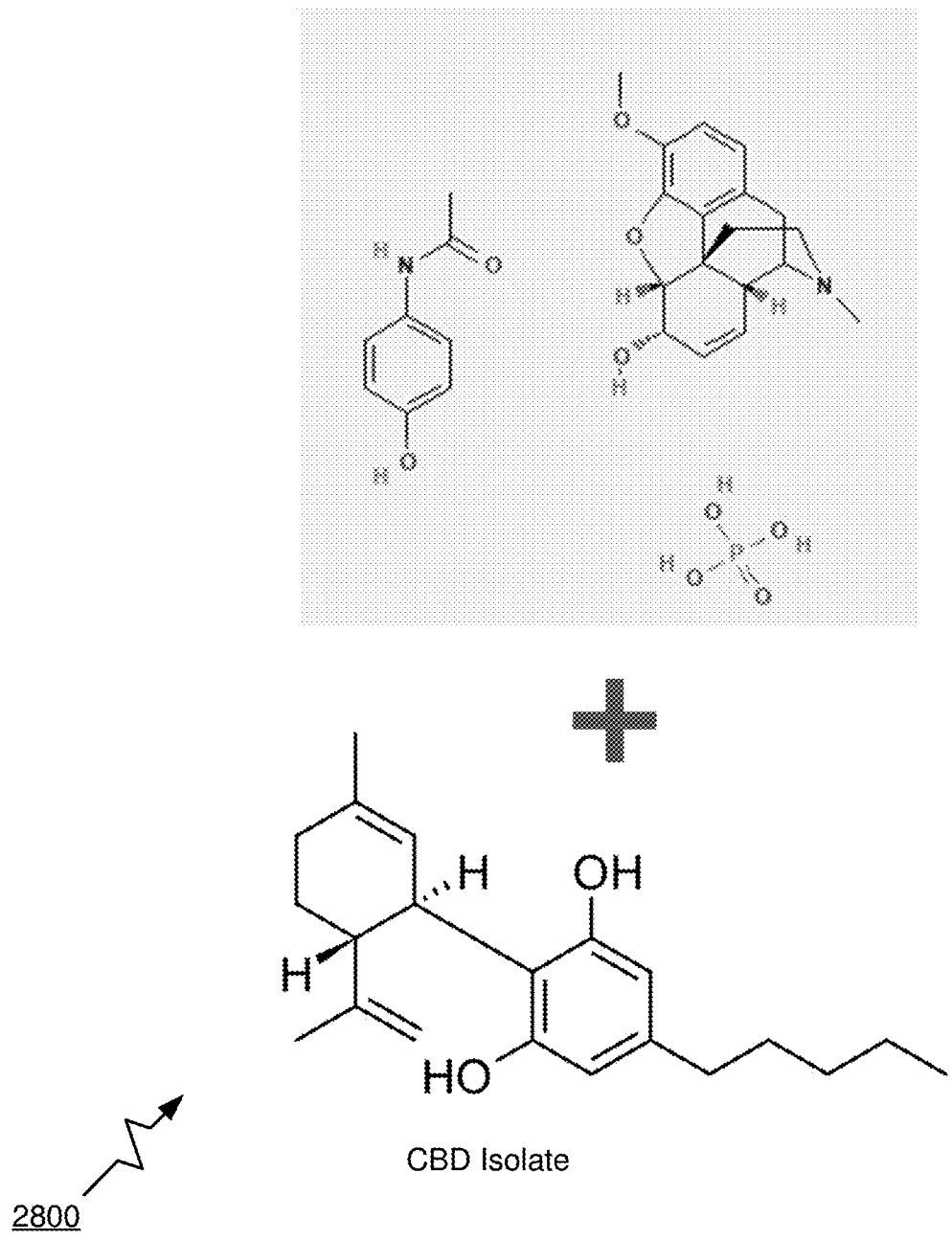
FIG. 28 illustrates the chemical structures of acetaminophen and codeine phosphate and the CBD isolate used to formulate the new composition in accordance with the present invention.

FIG. 28 at 2700 illustrates the chemical structures for Acetaminophen and Codeine Phosphate and CBD isolate. This is another example of an improved blend formulation created in accordance with the present invention to reduce the ill effects of this opioid blend. The blend formulation has only 0.25 of the active ingredients in Acetaminophen and Codeine Phosphate and CBD isolate and is blended with the processes described in FIGS. 1, 3, 4A, 4B, 5, 6, 7, and 8. It is named here as "Acetaminophen-Codeine-Phosphate/CBD Isolate Blend Composition."

Figure 29:
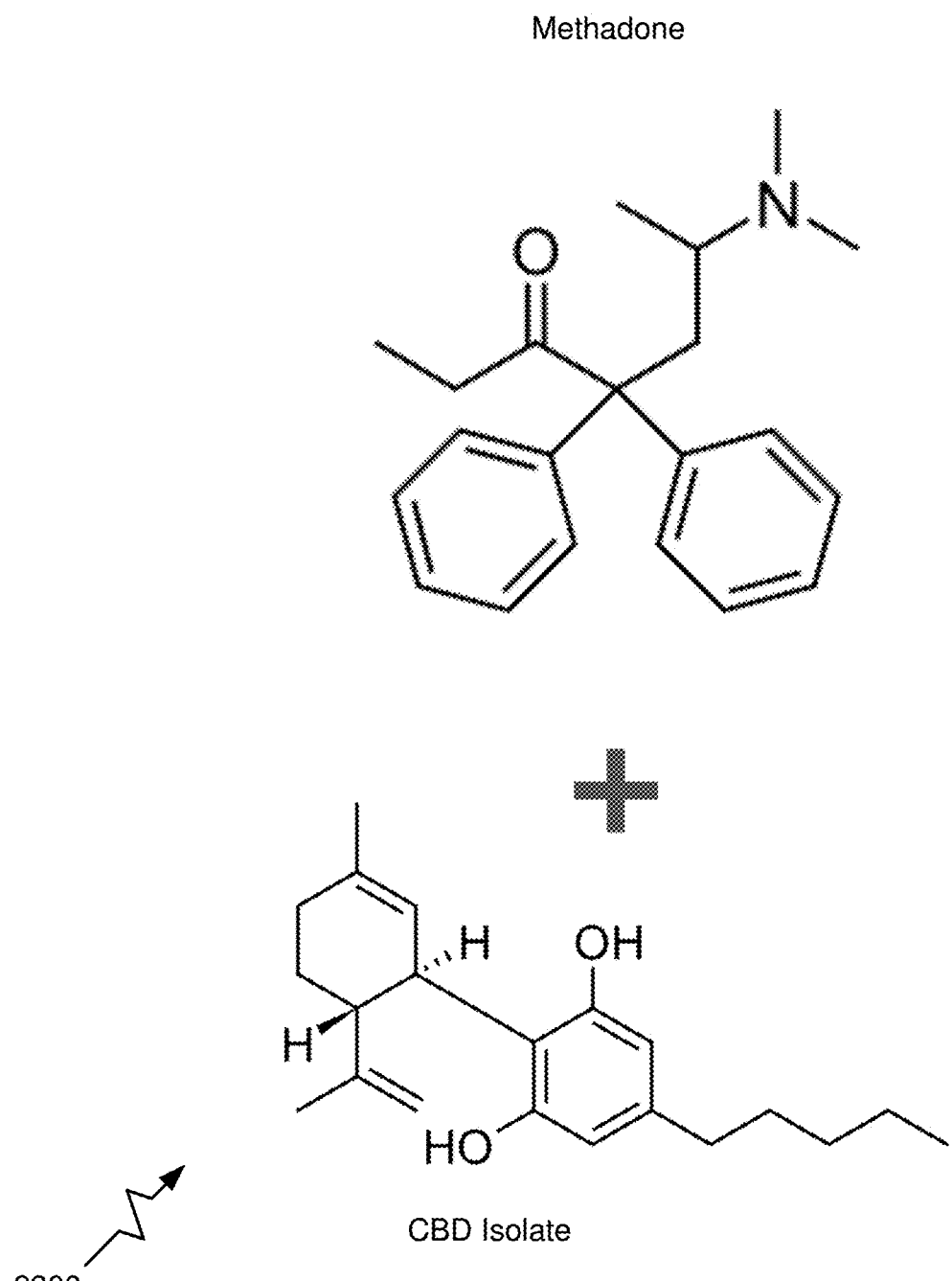
FIG. 29 illustrates the chemical structures of methadone and the CBD isolate used to formulate the new composition in accordance with the present invention.

FIG. 29 at 2900 illustrates the chemical structures for Methadone and CBD isolate. This is another example of an improved blend formulation created in accordance with the present invention to reduce the ill effects of this opioid blend. The blend formulation has only 0.25 of the active ingredients in Methadone and CBD isolate and is blended with the processes described in FIGS. 1, 3, 4A, 4B, 5, 6, 7, and 8. It is named here as "Methadone/CBD Isolate Blend Composition."

Figure 30:
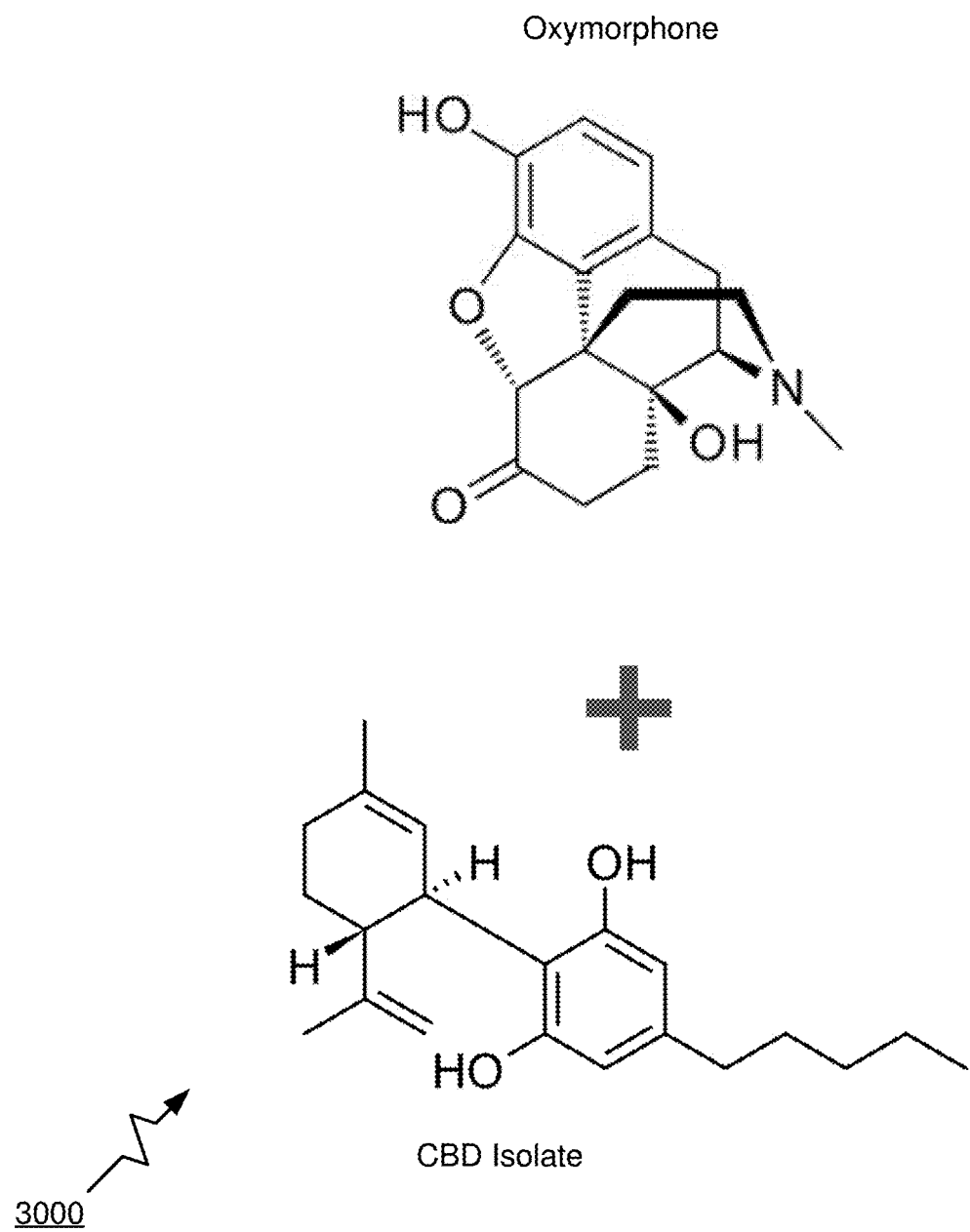
FIG. 30 illustrates the chemical structures of oxymorphine and the CBD isolate used to formulate the new composition in accordance with the present invention.

FIG. 30 at 3000 illustrates the chemical structures for Oxymorphone and CBD isolate. This is another example of an improved blend formulation created in accordance with the present invention to reduce the ill effects of this opioid blend. The blend formulation has only 0.25 of the active ingredients in Oxymorphone and CBD isolate and is blended with the processes described in FIGS. 1, 3, 4A, 4B, 5, 6, 7, and 8. It is named here as "Oxymorphone/CBD Isolate Blend Composition."

Figure 31:
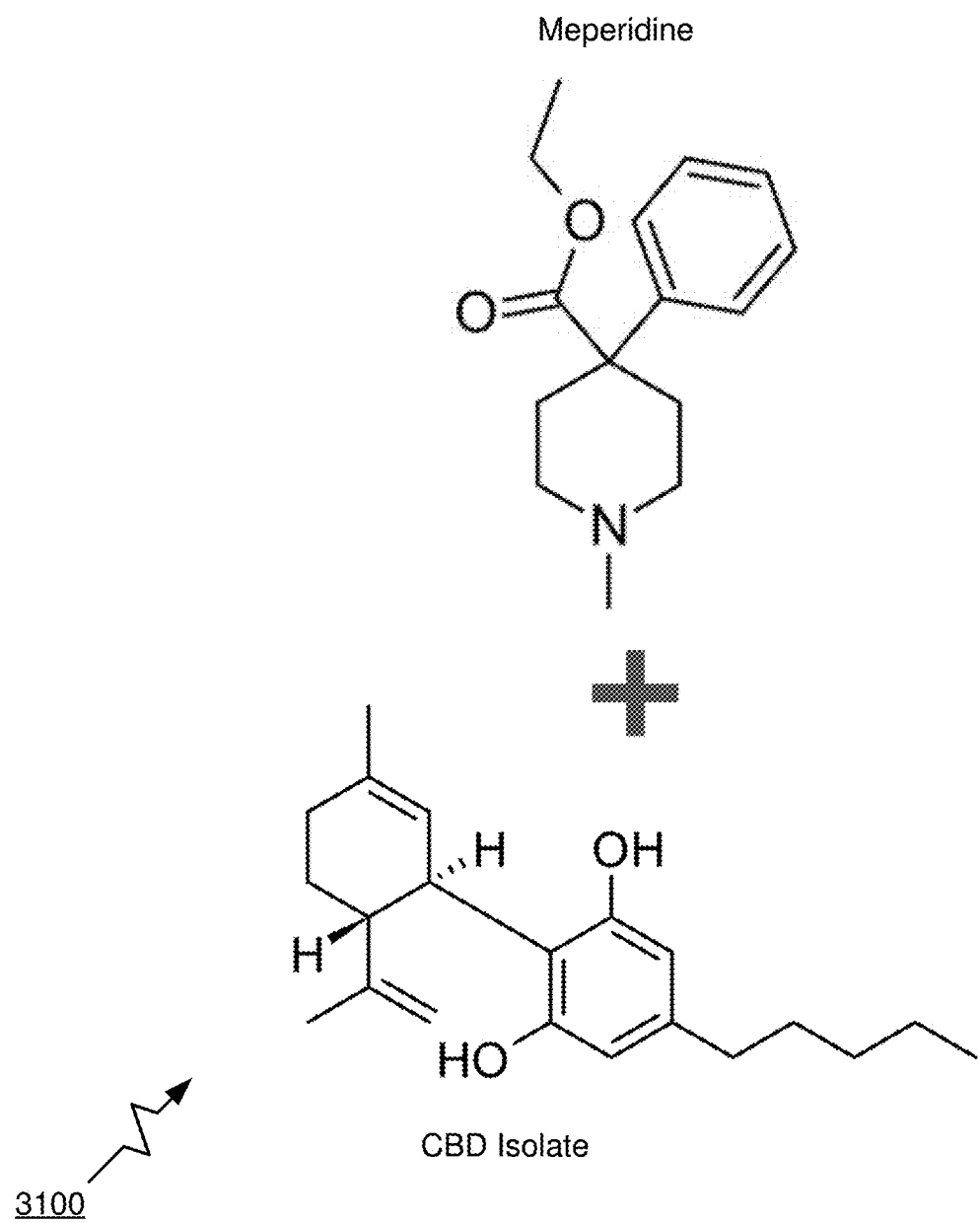
FIG. 31 illustrates the chemical structures of meperidine and the CBD isolate used to formulate the new composition in accordance with the present invention.

FIG. 31 at 3100 illustrates the chemical structures for Meperidine and CBD isolate. This is another example of an improved blend formulation created in accordance with the present invention to reduce the ill effects of this opioid blend at high potency levels. The blend formulation has only 0.25 of the active ingredients in Meperidine and CBD isolate and is blended with the processes described in FIGS. 1, 3, 4A, 4B, 5, 6, 7, and 8. It is named here as "Meperidine/CBD Isolate Blend Composition."

Figure 32:
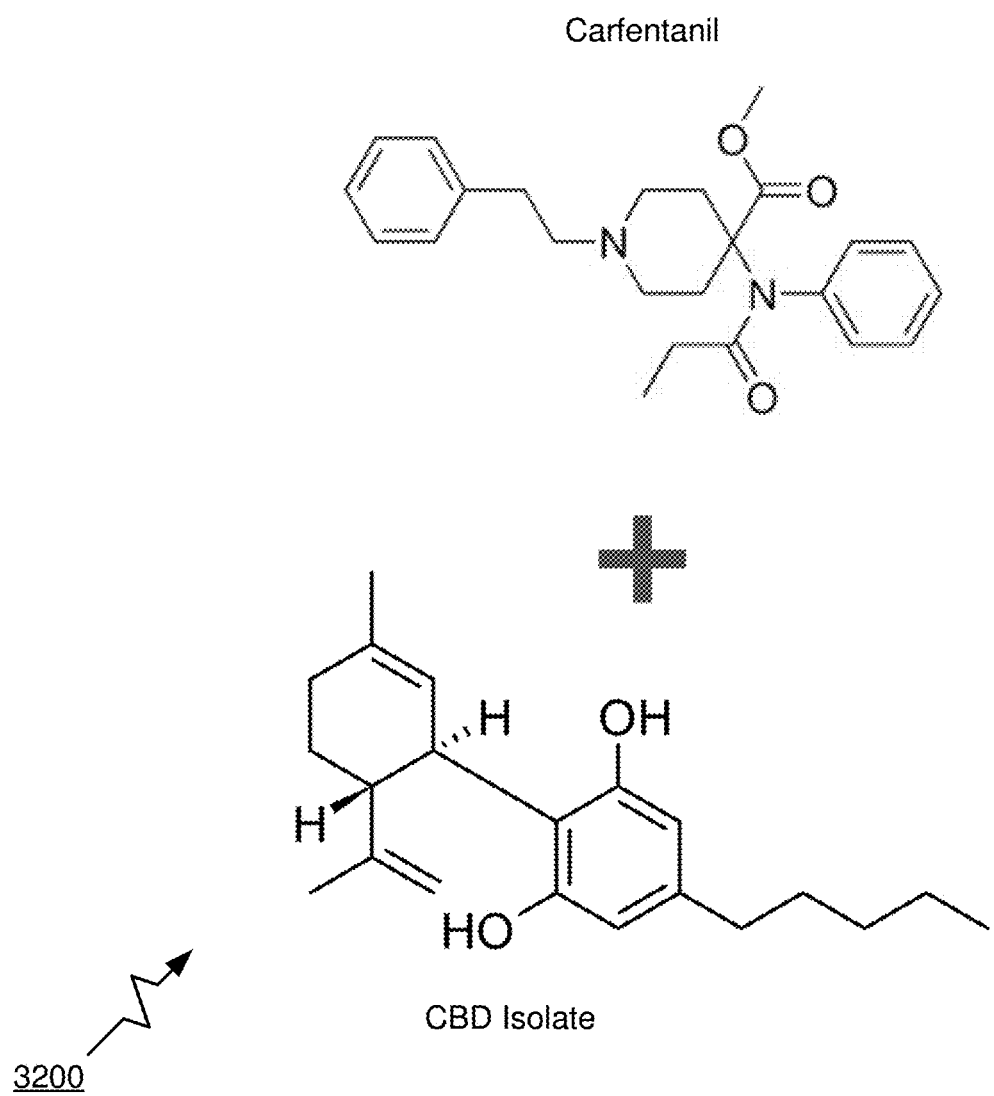
FIG. 32 illustrates the chemical structures of carfentanil and the CBD isolate used to formulate the new composition in accordance with the present invention.

FIG. 32 at 3200 illustrates the chemical structures for Carfentanil and CBD isolate. This is another example of an improved blend formulation created in accordance with the present invention to reduce the ill effects of this opioid blend at high potency levels. The blend formulation has only 0.25 of the active ingredients in Carfentanil and CBD isolate and is blended with the processes described in FIGS. 1, 3, 4A, 4B, 5, 6, 7, and 8. It is named here as "Carfentanil/CBD Isolate Blend Composition."

Figure 33:
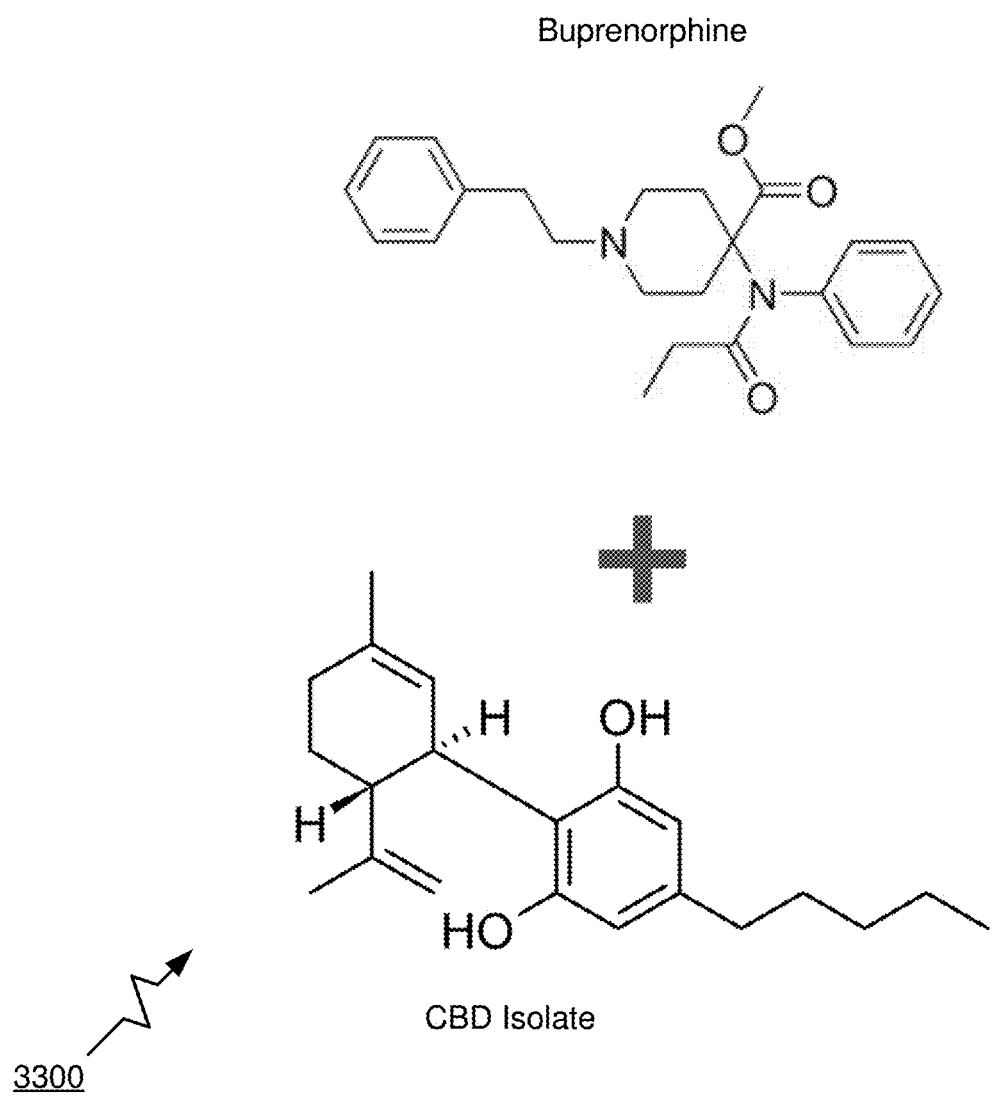
FIG. 33 illustrates the chemical structures of buprenorphine and the CBD isolate used to formulate the new composition in accordance with the present invention.

FIG. 33 at 3300 illustrates the chemical structures for Buprenorphine and CBD isolate. This is another example of an improved blend formulation created in accordance with the present invention to reduce the ill effects of this opioid blend at high potency levels. The blend formulation has only 0.25 of the active ingredients in Buprenorphine and CBD isolate and is blended with the processes described in FIGS. 1, 3, 4A, 4B, 5, 6, 7, and 8. It is named here as "Buprenorphine/CBD Isolate Blend Composition."

In the above description, for purposes of explanation, numerous specific details are set forth in order to provide a thorough understanding of the approach for amplifying the effects of pain-management without increasing the dosage of the active ingredient, and instead taking only a quarter amount by weight of synthetic active ingredients. It will be apparent, however, that this methodology can be practiced without some of these specific details. In other instances, structures and devices are shown in block diagram form in order to avoid obscuring the innovative aspects. For example, the present invention as illustrated may be implemented with computing devices with displays and processors for performing various tasks. Computing devices may be used to ensure accurate measurements of the ingredients and percentage of the various ingredients in the compositions. In some instances, computing devices and software may be used to track the various ingredients, any defects noted in batches of formulated products etc. In some instances, computer modeling tools may be used to simulate effects of the formulated products, compare effects with data compiled over time to refine ingredient amounts.

Reference in the specification to "one implementation, instance, or embodiment" or "an implementation or embodiment" simply means that a particular feature, structure, or characteristic described in connection with the implementation or embodiment is included in at least one implementation or embodiment of the present invention described. The appearances of the phrase "in one implementation, instance, or embodiment" in various places in the specification are not necessarily all referring to the same implementation, instance, or embodiment.

While preferred embodiments of the present invention have been shown and described herein, it will be obvious to those skilled in the art that such embodiments are provided only by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The term "about" or "nearly" as used herein refers to within +/−2% or 1% of the designated amount.

The foregoing description of the embodiments of the present invention has been presented for the purposes of illustration and description. It is not intended to be exhaustive or to limit the present invention to the precise form disclosed. Many modifications and variations are possible in light of the above teaching. It is intended that the scope of the present inventive processes and compositions be limited not by this detailed description, but rather by the claims of this application. As will be understood by those familiar with the art, the present inventive compositions and processes may be embodied in other specific forms without departing from the spirit or essential characteristics thereof. Likewise, the particular naming and division of the processes, routines, features, attributes, methodologies and other aspects are not mandatory or significant, and the mechanisms that implement the present invention or its features may have different names, divisions and/or formats. Furthermore, as will be apparent to one of ordinary skill in the relevant art, the features, attributes, methodologies and other aspects of the present. Accordingly, the disclosure of the present invention is intended to be illustrative, but not limiting, of the scope of the present invention, which is set forth in the following claims.

What is claimed is:

1. A method of amplifying one or more effects of acetaminophen in a medication, comprising:
   i) providing 0.25 mg of an approved or prescribed amount of acetaminophen within a range of 325 mg to 3000 mg;
   ii) preparing an excipient at a temperature within a range of 30 degrees Celsius to 50 degrees Celsius wherein the excipient is at least one of a polyethylene glycol, a polysorbate 80/60/100, an olive oil, hemp seed oil, grape seed oil, and a medium-chain triglycerides oil;
   iii) introducing a natural CBD isolate in the amount of 100 mg to 500 mg;
   iv) blending the acetaminophen and the CBD isolate in the excipient at a temperature between 30-60 degrees Celsius into a formulated composition; and
   v) encapsulating or forming a tablet with the formulated composition for dispensing.

2. A method of amplifying one or more effects of naproxen or naproxen sodium in a medication, comprising:
   measuring and providing a quarter amount of at least one of 100 mg-1500 mg of naproxen and 220 mg-1500 mg of naproxen sodium;
   preparing an excipient at a temperature within a range of 30 degrees Celsius to 50 degrees Celsius, wherein the excipient is at least one a polyethylene glycol, a polysorbate 80/60/100, an olive oil, hemp seed oil, grape seed oil, and a medium-chain triglycerides oil;
   introducing a natural CBD isolate in the amount of 100-500 mg;
   blending at least one of the quarter amount of 100 mg-1500 mg of naproxen and the quarter amount of 220 mg-1500 mg of naproxen sodium and the CBD isolate in the excipient at a temperature between 30-60 degrees Celsius into a formulated composition;
   adding an additional ingredient into the formulated composition, wherein the additional ingredient is within 0.001% to 20% selected from a group consisting essentially of: 5-HTP (5-hydroxytryptophan), L-Theanine, Melatonin, Vitamin B6, Zinc, Magnesium (Glycinate, biglycinate, or oxide), Jujube seed powder, Ashwagandha, Phosphatidyle Serine, Phospholipids, Huperzine, Lecithin, Willow Bark extract (Salacin), Ginsenosides, Bacopa, Gingko Biloba, Cannabinoids including Cannabinol, Cannabidiolic Acid, Cannabigerol, and Cannabigerolic Acid, Tetrahydrocannabinolic Acid, and Terpenes including Myrcene, Limonene, Beta Caryophyllene, Linalool, B-Pinene, Camphene, Eucalyptol, Humulene, and Geraniol; and encapsulating or forming a tablet with the formulated composition for dispensing.

3. A method of amplifying one or more effects of an opioid-related synthetic in a medication, comprising:

measuring and providing a quarter amount by weight of the opioid-related synthetic ingredient that is no more than 288 mg selected from a group consisting essentially of: Oxycodone, Hydrocodone-Acetaminophen, Hydrocodone bitartrate, Hydrocodone-Homatropine, Hydrocodone-Ibuprofen, Pseudoephedrine-Hydrocodone, Hydrocodone-Chlorpheniramine, Hydrocodone-Chlorpheniramine-Pseudoephedrine, Morphine, Morphine-Naltrexone, Hydromorphone, Fentanyl Citrate, Fentanyl, Codeine Polistirex-Chlorpheniramine Polistirex/CBD Isolate Composition, Acetaminophen and Codeine Phosphate, Methadone, Oxymorphone, Meperidine, Carfentanil, and Buprenorphine;

preparing an excipient at a temperature within a range of 30 degrees Celsius to 50 degrees Celsius, wherein the excipient is at least one of a polyethylene glycol, a polysorbate 80/60/100, an olive oil, hemp seed oil, grape seed oil, and a medium-chain triglycerides oil;

introducing a natural CBD isolate in the amount of 100-500 mg;

blending the quarter amount of the opioid-related synthetic ingredient and the CBD isolate in the excipient at a temperature between 30-60 degrees Celsius to formulate a composition;

adding an additional ingredient into the composition, wherein the additional ingredient is within 0.001% to 20% selected from a group consisting essentially of: 5-HTP (5-hydroxytryptophan), L-Theanine, Melatonin, Vitamin B6, Zinc, Magnesium (Glycinate, biglycinate, or oxide), Jujube seed powder, Ashwagandha, Phosphatidyle Serine, Phospholipids, Huperzine, Lecithin, Willow Bark extract (Salacin), Ginsenosides, Bacopa, Gingko Biloba, Cannabinoids including Cannabinol, Cannabidiolic Acid, Cannabigerol, and Cannabigerolic Acid, Tetrahydrocannabinolic Acid, and Terpenes including Myrcene, Limonene, Beta Caryophyllene, Linalool, B-Pinene, Camphene, Eucalyptol, Humulene, and Geraniol; and encapsulating or forming a tablet with the formulated composition for dispensing.

4. The method of amplifying the effects of acetaminophen in the medication according to claim 1, further comprising:

adding an additional ingredient into the formulated composition, comprising 0.001% to 20% selected from a group consisting essentially of: 5-HTP (5-hydroxytryptophan), L-Theanine, Melatonin, Vitamin B6, Zinc, Magnesium (Glycinate, biglycinate, or oxide), Jujube seed powder, Ashwagandha, Phosphatidyle Serine, Phospholipids, Huperzine, Lecithin, Willow Bark extract (Salacin), Ginsenosides, Bacopa, Gingko Biloba, Cannabinoids including Cannabinol, Cannabidiolic Acid, Cannabigerol, and Cannabigerolic Acid, Tetrahydrocannabinolic Acid, and Terpenes including Myrcene, Limonene, Beta Caryophyllene, Linalool, B-Pinene, Camphene, Eucalyptol, Humulene, and Geraniol.

5. The method of amplifying the effects of acetaminophen in the medication according to claim 1, wherein the excipient is the polyethylene glycol.

6. The method of amplifying the effects of acetaminophen in the medication according to claim 1, further comprising:

adding a designated amount of a preservative into the formulated composition, selected from a group consisting essentially of: Povidone, Tocopherol (Vitamin E), BHA (butylatedhydroxyanisole), BHT (butylatedhydroxytoulene), propyl gallate, citric acid, methyl paraben, ethyl paraben, propyl paraben, butyl paraben, benzyl alcohol, chlorobutanol, phenol, meta cresol, chloro cresol, benzoic acid, sorbic acid, thiomersal, phenylmecuric nitrate, bronopol, propylene glycol, benzylkonium chloride, and benzethonium chloride.

7. The method of amplifying the effects of acetaminophen in the medication according to claim 6, wherein the designated amount of the preservative is minimal.

8. The method of amplifying the effects of an opioid-related synthetic in the medication according to claim 3 further comprising:

adding a designated amount of a preservative into the composition, selected from a group consisting essentially of: Povidone, Tocopherol (Vitamin E), BHA (butylatedhydroxyanisole), BHT (butylatedhydroxytoulene), propyl gallate, citric acid, methyl paraben, ethyl paraben, propyl paraben, butyl paraben, benzyl alcohol, chlorobutanol, phenol, meta cresol, chloro cresol, benzoic acid, sorbic acid, thiomersal, phenylmecuric nitrate, bronopol, propylene glycol, benzylkonium chloride, and benzethonium chloride.

9. The method of amplifying the effects of the opioid-related synthetic in the medication according to claim 8, wherein the designated amount of preservative is minimal.

10. The method of amplifying the effects of acetaminophen in the medication according to claim 1, wherein the excipient is selected from a group consisting essentially of: the olive oil, h hemp seed oil, the grape seed oil, the medium-chain triglycerides oil.

11. A method of amplifying effects of ibuprofen or aspirin in a medication, comprising:

measuring and providing a quarter amount of 50 mg-3200 mg of ibuprofen or 50 mg-6000 mg of aspirin;

preparing an excipient at a temperature within a range of 30 degrees Celsius to 50 degrees Celsius, wherein the excipient is at least one of a polyethylene glycol and a polysorbate 80/60/100;

introducing a natural CBD isolate in the amount of 100-500 mg;

blending the quarter amount of 50 mg-3200 mg of ibuprofen or the quarter amount of 50 mg-6000 mg of aspirin and the CBD isolate in the excipient at a temperature between 30-60 degrees Celsius into a formulated composition;

adding an additional ingredient into the formulated composition, wherein the additional ingredient is within 0.001% to 20% selected from a group consisting essentially of: 5-HTP (5-hydroxytryptophan), L-Theanine, Melatonin, Vitamin B6, Zinc, Magnesium (Glycinate, biglycinate, or oxide), Jujube seed powder, Ashwagandha, Phosphatidyle Serine, Phospholipids, Huperzine, Lecithin, Willow Bark extract (Salacin), Ginsenosides, Bacopa, Gingko Biloba, Cannabinoids including Cannabinol, Cannabidiolic Acid, Cannabigerol, and Cannabigerolic Acid, Tetrahydrocannabinolic Acid, and Terpenes including Myrcene, Limonene, Beta Caryophyllene, Linalool, B-Pinene, Camphene, Eucalyptol, Humulene, and Geraniol; and encapsulating or forming a tablet with the formulated composition for dispensing.

* * * * *